United States Patent [19]
Aso et al.

[11] Patent Number: 5,965,874
[45] Date of Patent: Oct. 12, 1999

[54] METHOD AND APPARATUS FOR MEASURING THE POLARIZATION CHARACTERISTICS OF OPTICAL TRANSMISSION MEDIUM

[75] Inventors: Osamu Aso; Isamu Ohshima, both of Ichihara; Haruki Ogoshi, Chiba, all of Japan

[73] Assignee: The Furukawa Electric Co., Ltd., Tokyo, Japan

[21] Appl. No.: 08/807,870

[22] Filed: Feb. 26, 1997

Related U.S. Application Data

[63] Continuation of application No. PCT/JP96/01786, Jun. 27, 1996.

[30]     Foreign Application Priority Data

Jun. 30, 1995  [JP]  Japan ..................................... 7-187837
Jun. 30, 1995  [JP]  Japan ..................................... 7-187838

[51] Int. Cl.$^6$ ................................ G02F 1/01; G01J 4/00
[52] U.S. Cl. ..................... 250/225; 250/227.17; 356/364
[58] Field of Search .............................. 250/225, 227.17; 356/364, 365, 366, 367, 73.1

[56]            References Cited

U.S. PATENT DOCUMENTS

| | | | |
|---|---|---|---|
| 5,227,623 | 7/1993 | Heffner | 250/225 |
| 5,298,972 | 3/1994 | Heffner | 356/364 |

FOREIGN PATENT DOCUMENTS

| | | |
|---|---|---|
| 5-209791 | 9/1992 | Japan . |
| 5-273082 | 1/1993 | Japan . |
| 6-235880 | 2/1993 | Japan . |

OTHER PUBLICATIONS

Polarization Mode Dispersion and its Effect on Optical Transmission 1993. J.J. Refi NCTA Technical Papers. p 116–212.

Phenomenological Approach to Polarization Dispersion in Long Single–Mode Fibers Electronic Letters, Sep. 11, 1986. vol. 22, No. 19.
Automated Measurement of Polarization Mode Dispersion Using Jones Matrix Eigenanalysis. B.L. Heffner. IEEE Photonics Technology, vol. 4, No. 9 Sep. 1992.
Polarization evolution and dispersion in fibers with spatially varying birefringence. C.R. Menyuk and P.K.A. Wai 1994 Optical Society of America vol. 11, No. 7, Jul. 1994.
Polarization mode dispersion: time versus frequency domains. N. Gisin and J.P. Pellaux Optics Communications 89 (1992) 316–323, May 1, 1992.
Study on A Conservation Quantity in PMD Measurements Technical Digest–Symposium Fiber Measurement 1994, pp. 159–162.
Wavelength dependence of birefringence in single–mode fiber. W. Eickhoff, Y. Yen and R. Ulrich Applied Optics, vol. 20, No. 19, Oct. 10, 1981.

*Primary Examiner*—Edward P. Westin
*Assistant Examiner*—Kevin Pyo
*Attorney, Agent, or Firm*—Lacasse & Associates; Randy W. Lacasse; Wesley L. Strickland

[57]            ABSTRACT

A method to obtain polarization characteristics of an optical transmission medium is disclosed. Sequentially plural different states of polarized light are launched into the optical transmission medium. Intensities of light emerging from the optical transmission medium through combinations of optical elements are measured to obtain Stokes parameters from which Stokes vectors describing the emerging light corresponding to each of the plural sequentially launched states of polarization are obtained; for at least three different launched states of polarization, descriptors are used of these launched states of polarization and the Stokes vectors describing the corresponding emerging light to calculate a Jones matrix which mathematically models the changes that the launched light when described in terms of a Jones vector is subject to when passing through the optical transmission medium; and, the Jones matrix is used to describe the polarization characteristics of the optical transmission medium.

19 Claims, 5 Drawing Sheets

• front surface on the sphere
○ back surface on the sphere

METHOD AND APPARATUS FOR MEASURING THE POLARIZATION CHARACTERISTICS OF OPTICAL TRANSMISSION MEDIUM

This application is a continuation of application PCT international application No: PCT/JP96/01786 filed Jun. 27, 1996.

FIELD OF THE INVENTION

The present invention relates to a method and apparatus for measuring polarization properties of an optical transmission medium and the state of polarization of light that has passed through such medium, generally in the industrial field utilizing the polarization optics. More particularly, the invention expands this method and apparatus to the accurate estimation of the differential group delay time of the principal states of polarization which is one of the more important parameters characterizing polarization mode dispersion and one that limits transmission capacity of optical fibres in the field of optical communications.

BACKGROUND OF THE INVENTION

It is well known that the Mueller analysis and the Jones analysis are useful in the study of polarization optics especially relating to the state of polarization of light and polarization properties of an optical transmission medium 18. (reference [18]) Note that a list of the books and literature is referred to in this specification and is shown in Table 3 which is at the end of his specification. The advantage in using the Jones analysis is its simplicity. In spite of the fact that one can study, in principle, only perfectly polarized light in the framework of the Jones analysis, the analysis provides a simple approach compared to the other methods, e.g., Mueller's analysis. The reason for this more simplistic approach comes from the fact instead of using larger 4×4 or 3×3 matrices as in Mueller's analysis, one uses 2×2 matrices for the Jones analysis. The mathematical relation between the Jones' and Mueller's analysis has been studied by Takenaka in 1972 (reference [1]) and is summarized as the difference of the representation of the rotational group. When the polarization dependent loss in of a transmission media is negligible, the elements of the Mueller and Jones matrices are understood as the rotational operator. Concretely, the representations of the rotational group these matrices is known to be a three dimensional orthogonal group: O(3) and the special unitary group: SU(2). These two groups are transformed as a homomorphism mapping. The result of the comparison between the Jones analysis and the Mueller analysis is shown in Table 1. So far, in spite of the advantages explained above, most experimental study of polarization optics is achieved using the Mueller's analysis. Reasons of this dominance of the Mueller's analysis in experimental polarization optics are summarized as follows: (i) in the vector representing the light, a Stokes vector, the parameters represent optical intensities and are directly measurable quantities.(reference [1]) (ii) the Poincaré sphere representation of a Stokes vector provides an intuitive way for understanding polarization. However, it is widely known that both the Jones method and Mueller's method have advantages and disadvantages relative to each other. Thus, in some instances, and in practical situations, one can approach the problem in two ways.

TABLE 1

|  | Jones' Analysis | Mueller's Analysis |
| --- | --- | --- |
| Description of the state of polarization | Two dimensional complex spinors: Jones vector | Four or three dimensional real vectors: Stokes vector |
| Description of the optical transmission media in case when the polarization dependent loss is negligible | 2 × 2 complex matrices: Jones matrices | 4 × 4 or 3 × 3 real matrices: Mueller matrices |
| Whether the state of polarization is possible to determine directly or not? | Impossible | Possible |
| Theoretical Analysis | Comparatively easy | Complicated |

Based on the original work by Jones (reference [3],[4]), we will briefly review the conventional matrix measurement method. For the purpose of the matrix determination experimentally, we utilize a 2×2 complex Jones matrix as follows:

$$\mu = \begin{bmatrix} \eta_1 & \eta_2 \\ \eta_3 & \eta_4 \end{bmatrix} = \begin{bmatrix} \eta_1/\eta_4 & \eta_2/\eta_4 \\ \eta_3/\eta_4 & 1 \end{bmatrix} = \beta \begin{bmatrix} k_1 k_4 & k_2 \\ k_4 & 1 \end{bmatrix}. \quad (15)$$

From which $$\eta_4 = \beta. \quad (16.1)$$

$$\eta_2 = \beta k_2 \quad (16.2)$$

$$\eta_3 = \beta k_4 \quad (16.3)$$

$$\eta_1 = \beta k_1 k_4 \quad (16.4)$$

Then the estimation of $\eta_i$ (i=1, 2, 3, 4) provides the 4 matrix elements. According to Jones, one measures the output electrical fields corresponding the following three incident states of polarization, represented by the Jones vectors as:

$$\xi_A = \begin{bmatrix} 1 \\ 0 \end{bmatrix}, \xi_B = \begin{bmatrix} 0 \\ 1 \end{bmatrix}, \xi_C = \frac{1}{\sqrt{2}} \begin{bmatrix} 1 \\ 1 \end{bmatrix} \quad (17)$$

The output state of polarization corresponding to the above three vectors are represented as $$h = \begin{bmatrix} h_1 \\ h_2 \end{bmatrix}, v = \begin{bmatrix} v_1 \\ v_2 \end{bmatrix}, q = \begin{bmatrix} q_1 \\ q_2 \end{bmatrix} \quad (18)$$

Then the Jones calculus provides the following relations $$k_1 = h_1/h_2 \quad (19.1)$$

$$k_2 = v_1/v_2 \quad (192)$$

$$k_3 = q_1/q_2 \quad (193)$$

$$k_4 = (k_3 - k_2)/(k_1 - k_3) \quad (19.4)$$

The right hand side of these equations are represented as ratios of electric fields, and in principle are measurable quantities from which the matrix elements can be determined experimentally using the relation shown in eqs.(19) and thereafter eqs.(16). For the above discussions, the Jones matrix measurement scheme proposed by R. C. Jones in 1947 has been reviewed This measurement scheme has been utilized until now.

In the field of the optics, accurate determination of the Jones matrix makes it possible to analyze the polarization properties of some transmission media and therefore is important. In the field of the optical communications, and particularly with recent developments in optical amplifier systems, an accurate measurement of the differential group delay (hereafter referred as DGD) of the principal states of polarization (referred as PSP) is required. For this, it is necessary to know the polarization mode dispersion (PMD) characteristics of the single-mode optical fibres being utilized (references [4] and [6])

In general, it is known that the Jones matrices for an arbitrary transmission medium have the following characteristics:

(1) In case where polarization dependent loss of the medium is negligible, the Jones matrix is written in the following form (reference[6])

$$T = exp(\rho)U \tag{20}$$

where P is the medium independent loss or the state of polarization of light, and U (reference[20]) can be written as:

$$U = \begin{bmatrix} u_1 & u_2 \\ -u_2^* & u_1^* \end{bmatrix}, det\ U = +1 \tag{21}$$

where the asterisk represents the complex conjugate.

(2) In the case where the transmission medium is stable, both spatially and over time, it is possible to separate a diagonal matrix which represents the linear birefringence and the effect of the circular birefringence, through a suitable unitary transformation.

(3) In case where the polarization dependent losses of the transmission medium are finite and not negligible, the determinant of the matrix U is smaller than the unity.

From the above discussions, it can be seen that the Jones matrix representation of the medium is useful for the analysis of cases where the degree of polarization (DOP) of the transmitted lightwave is almost unity and the polarization dependent loss(PDL) of the medium are negligible. In this situation, Jones matrix elements can be described as shown in Equations 20 and 21. Based on the unimodular unitary properties of the matrix, Poole and Wagner have derived the concept of the PSP and it is now regarded that the concept plays a fundamental role in polarization mode dispersion analysis (reference[6]). Recently Aso and his colleagues have derived a theoretical formula for polarization mode dispersion measurement using a wavelength scanning method (refercnces[7]). The formula has been confirmed experimentally by using an optical fibre that consists of two polarization maintaining fibres with fmite angular misalignment. In the derivation of the formula the uniitarity characteristics of the Jones matrix have been utilized.

In relation to long haul optical communication systems having optical amplifiers and dispersion shifted fibres, or alternatively conventional single-mode fibres with dispersion compensated fibres, PMD is considered to be an important parameter which limits the transmission capacity of the system. In reference [23] the origins of polarization mode dispersion are summarized. These origins consist of intrinsic and external causes, where the external causes refer to those affects on the optical fibre which originate during cable installation. However, in practice, these causes are randomly distributed along the length of the fibre and the state of the polarization mode coupling changes with time (reference [2]). In such cases local polarization modes are coupled along the fibre and therefore the concept of the eigen states of polarization is not a viable form of analysis. This situation is called random mode coupling. Random mode coupling makes it difficult to analyze the precise nature of the polarization properties of the optical fibre. In such cases, instead of using the eigen states of polarization, the concept of the PSP is a viable form of analysis (reference[8]). Poole and Wagner have proposed a rigorous PMD evaluation method. They have proved the existence of the PSPs (principal states of polarization) both theoretically and experimentally (reference[22]) and have shown that the DGD time of the PSPs is one of the most important parameters in PMD analysis. Based on their results, B. L. Heffnier has reported a novel measurement technique for estimating the DGD time of the PSPs (reference [4]). This method is referred to as the Jones matrix eigenanalysis (hereafter JME). According to the report from N. Gisin, JE is regarded to as one of the most precise measurement techniques (reference[24]).

In the following discussions, we will briefly review the concept of the PSP and the measurement technique of the DGD time of PSPs. Then we shall consider the problem of the proposed DGD time estimation method. As shown in references [1],[9] and [25] and references therein, the SOP changes along the optical transmission medium and is governed by the equation of the rotational motion in the spinor field (reference[20]). According to the spinorial treatment, under the assumption of perfect polarization and the negligible PDL (polarization dependent loss), the transfer matrix of the medium can be written in the form of the following 2×2 unitary matrix(reference[6])

$$T = exp(i\rho)U = exp(i\rho)\begin{bmatrix} u_1 & u_2 \\ -u_2^* & u_1^* \end{bmatrix}, det\ U = +1 \tag{22}$$

where the asterisk represents the complex conjugate. In this representation, we assume that the optical losses that are independent of the state of polarization are neglected. However, as shown in reference [6], it is straightforward to extend the following discussions to cases which include the influences of the optical losses and it has been confirmed that the final result of the following discussions coincide. According to the Jones calculus, the relation between the incident state of polarization (SOP) and output SOP is written as $$\xi_{out} = exp(i\rho)U\ \xi_{out} \tag{23}$$

$$\xi_{in} = exp(-i\rho)U^+\xi_{in} \tag{24}$$

where + represents the henrite conjugate of the matrix and P is the absolute phase change through transmission of the medium. Taking derivatives of both sides of eq.(23) with respect to the angular frequency of light w and using the relation in eq.(24), provides the following equation $$\frac{d\xi_{out}}{d\omega} = \frac{dU}{d\omega}\xi_{in} - i\frac{d\rho}{d\omega}U\ \xi_{in} \tag{25}$$

Here the SOP of the incident light are fixed as $$\frac{d\xi_{in}}{d\omega} = 0 \tag{26}$$

As shown in reference [6], principal states of polarization are defined as the SOP that satisfies the following condition $$\frac{d\xi_{out}}{d\omega} = 0 \quad (27)$$

Then the eigenvalue equation is obtained from the relation shown in eq.(25)

$$\frac{dU}{d\omega}\xi_{in} - i\frac{d\rho}{d\omega}U\xi_{in} = 0 \quad (28)$$

The explicit form shown in eq.(22) will lead to the following eigenvalue and corresponding eigen Jones vectors $$\frac{d\rho\pm}{d\omega} = \pm\sqrt{\left|\frac{du_1}{d\omega}\right|^2 + \left|\frac{du_2}{d\omega}\right|^2} \quad (29)$$

The eigenvectors corresponding to these eigenvectors eigenvalues are orthogonal (reference[6]) and the vectors are called the incident PSPs (principal states of polarization). Output PSPs are obtained by operating the transfer matrix (22) on the incident PSPs, with the stability of the SOP with respect to frequency changes being first order. In order to satisfy the stability of the PSPS, the following conditions must be met:

$$\frac{d^n u_i}{d\omega^n} = O(e^n), (i = 1, 2), (n \geq 2) \quad (30.1)$$

$$\frac{du_i}{d\omega}\frac{du_j}{d\omega} = O(e^2), (i, j = 1, 2) \quad (30.2)$$

where O is the Landau operator and higher than second order quantities are neglected. Principal states of polarization are stable as long as the above conditions are satisfied in practical situations. In this sense, the existence of the PSP is a generalized concept of the eigen state of polaization (reference [1]). According to reference [6], the DGD (differential group delay) time of the PSPs $\Delta t$, are one of the most important parameters describing the PMD. The above expression for the PSP allows us to obtain the following result $$\Delta\tau = \left|\frac{d\rho_+}{d\omega} - \frac{d\rho_-}{d\omega}\right| = 2\sqrt{\left|\frac{du_1}{d\omega}\right|^2 + \left|\frac{du_2}{d\omega}\right|^2} \quad (31)$$

The above discussions provide a fundamental framework for PMD analysis based on the PSPs, and are provided as a theoretical background for PMD measurement using the Jones matrix eigenanalysis. One should note that the above DGD time estimation is correct when the conditions (27) are confirmed in the practical situations. In this sense, it is known that the above $\Delta t$ estimation is correct to the first order approximation (reference [6]).

For the purpose of this discussion, it is necessary to describe a brief review of another estimation method for the DGD time of PSPs. This method is based on Mueller analysis and sometimes referred as the Stokes parameter method (reference [31]). According to reference [20], measurement of the frequency dependence of the output Stokes vector on the Poincare sphere will allow an estimate the DGD time of PSPs to be made. For this, use will be made of the Stokes space (reference [25]) wherein the normalized Stokes vector defines the SOP space where the geometry of the space is three-dimensional Euclidian. In the following discussions, the normalized Stokes vector is referred to simply as the Stokes vector. The concept of PSP and the DGD time of PSPs represented in the SOP field will be reviewed.

Wavelength dependence of the Stokes vector has been studied by W. Eickhoff and his colleagues (reference [26]). They have proposed the following basic equation as an analogy of the spatial SOP change in the birefringent medium by Uhicb (reference[27]). They also confirmed their own results by experiment.

$$\frac{dS}{d\omega} = \Omega \times S \quad (32)$$

In this equation, S is the Stokes vector of the output SOP, $\omega$ is the angular frequency of light. $\Omega$ a vector in the Stokes space whose magnitude coincides with the DGD time of PSPs; the two intersects of the vector with the Poincare sphere represent the PSPs. Therefore the vector is referred as the polarization dispersion vector (reference [29]). In the original paper from Eickhoff et.al.(reference[26]), the transmission media have been considered for cases where the birefingence is homogeneous along the longitudinal direction. Recently, Poole et.al., have shown that the description shown in eq.(32) can be extended straightforwardly to the case where polarization mode coupling exists. Eq.(32) is in the same form as the equation of the rotational motion( e.g., Larmor precession shown in reference[32]). Then the Stokes vector rotates on the Poincare sphere along n if the polarization dispersion vector is independent of the wavelength.

As discussed previously, the original Jones matrix estimation method developed by Jones is very sensitive to the unavoidable experimental errors that violate the symmetry properties of the matrix. Then the unitarity of the estimated matrix is generally violated. Principally the reason of the symmetry breaking could be considered as follows:(a) According to the original method, matrix elements are determined individually; then the unavoidable measurement error directly influences the results, (b)When the PDL (polarization dependent losses) of the medium are not perfectly neglected, the effect of PDL violates the symmetry of the matrix, (e) Degradation of the DOP (degree of polarization) of the output light makes it difficult to maintain consistency between experiments and theory. The matrix symmetry breakdown causes difficulties in obtaining certain important information related to the birefringence of the medium.

As discussed previously, Poole and Wagner have derived the concept of PSP (principal state of polarization ) based on the Jones analysis. According to their results, B. L. Heffner developed the PMD estimation technique (reference[4]). According to Heffhier, he has estimated the Jones matrix using the same approach as the original matrix estimation method (reference[3]). Thus, he could not avoid the matrix symmetry breaking down. However, in order to avoid the difficulties, Heffner has introduced another eigenvalue equation based on a exponential approximation (reference [4]). However since the original PSP theory does not demand his exponential approximation, the following problem has remained: Is the exponential approximation consistent with the first order approximation of the PSP or not? Aso and his colleagues have investigated the difference of the first order approximation region and the exponential approximation region in the wavelength domain. Results of their study using an 80km length dispersion shifted single-mode optical fibre showed that any differences between the sufficient condition of these two approximations could not be found in the frequency domain measurements (reference [10],[11]). However their discussions were never extended straightforwardly to the general case. Thus the importance of maintaining the Jones matrix symmetry is noted in this specification.

As described heretofore, B. L. Heffner has published a design of the PMD measurement system based on the concept of the principal state of polarization (reference [4]). The method is referred as the Jones matrix eigenanalysis. A summary is now provided of the measurement scheme proposed by Hefffier. Firstly, three different SOPs (States of Polarization) with angular frequency $\omega_o$ are launched into a transmission medium under test. Then information of the corresponding output SOP leads us to determine every Jones matrix component of the medium uniquely according to the scheme shown in the previous discussions (reference [3]). According to Heffner, one can construct a characteristic finite differential equation corresponding to the eigenvalue equation (28) from the information of the Jones matrix measured at two frequencies with finite interval $\Delta\omega$, say at $\omega_o$ and $\omega_o+\Delta\omega$. The solution of the finite differential equation allows the DGD (differential group delay) time of PSPs to be estimated. Within the framework of the first order approximation criteria, frequency step-size $\Delta\omega$ for the measurement is necessary in order to ensure the existence of the PSPs as the base vector in the Stokes space. However, in practice the measurement accuracy demands a large $\Delta\omega$. Nevertheless one can not distinguish the difference of the information between the measurements taken at two frequencies if the stepsize is too small. The above discussion indicates the existence of a suitable frequency stepsize for the PMD measurement from Jones matrix eigenanalysis, wherein a suitable frequency step-size is the largest step-size in which the PSP remains in the first order( reference[30]).

Incorrectly selecting the step-size apparently causes a DGD time mis-estimation. This phenomenon is noted in Hewlett Packard's polarization analyzer user's manual (reference[30]) and is also confirmed in experiments by Aso, etal. (reference[10],[11]). This drawback is considered as the most conspicuous in the Jones matrix eigenanalysis. A technique which has been developed in order to solve the above problem will now be discussed (reference [4],[5], [31]). The first step of this technique is to observe how the trajectory of the output SOP (state of polarization) changes with respect to the angular frequency of light. Based on the equation (32) and (33), the first order frequency change $\Delta\omega$ leads us to observe tie trajectory where the Stokes vector traces the arc of a complete circle as shown in FIG. 5. If the choice of the frequency step-size $\Delta\omega$ is larger than the "suitable" stepsize, the trajectory runs off the arc of the above reference circle. The suitable stepsize can thus be estimated as the largest frequency step-size where the observed Stokes vector trajectory is on the circle (reference [10]). However, the exact proof that the estimated DGD (differential group delay) time of PSPs (principal states of polarization) using the above $\Delta\omega$ by the Jones matrix eigenanalysis seems to have not been given.

According to the Jones matrix eigenanalysis approach reported in reference [4]and[5], the transmission matrix is determined by the original method proposed by R. C. Jones (reference[3]). However, the negligibly small PDL (polarization dependent losses) of the medium and the unavoidable measurement errors may violate the unitarity of the estimated matrix.

Heffner has derived the eigenvalue equation that differs from equation (28); in his equation two eigenvalues coincide with the DGD time of PSPs. His equation is ingenious and the constraint of the matrix symmetry does not explicitly appear. Furthermore he has introduced exponential approximation which did not appear in the original paper (reference [6]). The exponential approximation leads to a convenient analysis. However the scheme seems to have no relation with the first order approximation. Aso and his colleagues have studied the difference of the exponential approximation with first order approximation in the PSP theory. They have measured the difference by using an 80 km dispersion shifted single mode optical fibre (reference [10],[11]). In these experiments, they found no difference between the two approximations. However, their experiments employed a transmission medium and no general proof was provided.

In order to determine a suitable wavelength step-size for PMD (polarization mode dispersion) measurement by Jones matrix eigenanalysis, Aso and his colleagues have proposed the comparison of global and local measurements (reference [11]). However, when one applies the idea to practical measurements, measurements over long durations of time are necessary to determine a suitable $\Delta\omega$ and the constraints from the local measurements limit the measurable DGD time of PSPs to less than 5 ps.

What follows is a summary of the causes of the drawbacks of the JME (Jones Matrix Eigenanalysis) method. (a) Measurement apparatus not made precisely according to the original PSP theory obtained by Poole and Wagner (reference [6]).(b) Since the original PSP theory is expressed within the framework of the Jones' calculus, in order to realize the measurements based on the theory, it is necessary to represent the explicit relation between the Jones vector and measurable quantities(e.g., Stokes parameters). Frequency dependence of the output SOP described by the Stokes vector is expressed by the eq.(32). The left hand side of eq.(32): $ds/d\omega$ corresponds to the derivative of the Jones vector with respect to the angular frequency. However to date the relationship between the eq.(32) and the corresponding equation expressed in the framework of the Jones' calculus seems not to have been analyzed precisely. (c) Also the relationship between the polarization dispersion vector $\Omega$ and the Jones matrix U has not yet been studied.

According to the Jones' calculus, the Jones vector representation of the output principal states is obtained by operating the Jones matrix on the incident Jones vector. The matrix is of 2×2 form. On the other hand, according to the Mueller's calculus, the output Stokes vector is obtained in a similar manner as the Jones calculus. However in this case the matrix is 4×4 and the number of matrix elements increase. Thus, the Jones calculus makes it easy to realize the calculation and obtain the output SOP. Jones vector measurements techniques which are consistent with the Stokes vector measurements have not yet been demonstrated.

OBJECTS AND SUMMARY OF THE INVENTION

The present invention has been made in view of the aforementioned circumstances and drawbacks. An object of the invention is to provide a method and an apparatus for obtaining the polarization characteristics of an optical transmission medium by evaluating the state of polarization of light and estimating the Jones matrix describing the birefringence and polarization mode coupling of the transmission medium while: a) making it clear how Jones vectors describing the state of polarization of light and Jones matrices describing the polarization properties of the transmission medium can be expressed utilizing the actually measurable Stokes parameters which have dimensions of the intensity of light; b) describing how Jones vectors may be expressed as functions of the normalized or the re-normalized Stokes vectors in cases where the degree of polarization of light is not equal to the unity and the polarization dependent losses of the medium are not negligible, being caused by unavoidable measurement errors; and c) expressing the Jones matrix in a way which conserves the unitarity of the matrix while utilizing the re-normalized Stokes vectors.

Another object of the invention is to apply the method of obtaining the polarization characteristics of an optical transmission medium to the measurent differential group delay time of the principal states of polarization characterizing polarization mode dispersion phenomenon by: a) estimating the direct polarization dispersion vector $\Omega$; b) rising simple and accurate measurement techniques for estimating the polarization dispersion vector of an optical transmission medium with high reliability; c) developing the relationship of the aforementioned equation(32), represented by the Stokes vector, to the corresponding equation when expressed within the framework of the Jones calculus; d) by expressing the Jones vectors, which represents the state of polarization of light in terms of the practically measurable Stokes parameters; and e) by making use of the measuring system based on the Jones analysis (to be followed experimentally), thereby making it possible to measure the polarization dispersion vector $\Omega$ without considering any other technique not explicitly included in the original idea of the principal states of polarization: e.g., the exponential approximation.

For a method for evaluating the state of polarization of light, the present invention consists of the following steps: Normalizing the Jones vector $$\psi = \begin{bmatrix} \psi_1 \\ \psi_2 \end{bmatrix}, \psi_i \in C, \text{ where } i = 1, 2 \quad (1)$$

as $$\xi = \begin{bmatrix} \xi_1 \\ \xi_2 \end{bmatrix} \equiv \frac{1}{\sqrt{\psi_1^2 + \psi_2^2}} \begin{bmatrix} \psi_1 \\ \psi_2 \end{bmatrix} \quad (2)$$

and similarly the Stokes vector $$S = \begin{bmatrix} I \\ Q \\ U \\ V \end{bmatrix} \quad (3)$$

can be normalized to form the normalized Stokes vector where by definition, $S_1=Q/I$, $S_2=U/I$ and $S_3=V/L$. When the measured lightwave is completely polarized, the components of the normalized Stokes vector satisfy the condition:

$$S_1^2+S_2^2+S_3^2=1 \quad (37)$$

Under this completely polarized condition, the relation between the normalized Stokes parameters can be expressed as the function of the Jones vector:

$$S_1=|\xi_1|^2-|\xi_2|^2 \quad (39a)$$

$$S_2=2Re(\xi_1\xi_2^*) \quad (39b)$$

$$S_3=2Im(\xi_1\xi_2^*) \quad (39c)$$

where Re[z] and Im[z] represents the real and imaginary part of z respectively. The normalized Jones vector may then be written in terms of the Stokes parameters as follows:

$$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2+iS_3 \end{bmatrix}, (S_1 \neq -1) \quad (4)$$

$$\xi = \begin{bmatrix} \xi_1 \\ \xi_2 \end{bmatrix} = \begin{bmatrix} 0 \\ 1 \end{bmatrix}, (S_1 = -1) \quad (5)$$

it is easily shown that the eq.(4) reduces to eq. (5) for the limiting condition of a singular SOP.

$$\xi = \lim_{s_1 \to -1} \frac{\exp(i\gamma)}{\sqrt{2(1+S_1)}} \begin{bmatrix} 1+S_1 \\ S_2+iS_3 \end{bmatrix} = \exp(i\gamma)\begin{bmatrix} 1 \\ 0 \end{bmatrix} \quad (6)$$

Thus we can summarize the Jones vector representation as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2+iS_3 \end{bmatrix} \quad (7)$$

In a preferred form of the aforementioned Stokes vector method for evaluating a state of polarization of light, the normalized Stokes parameters; $S_1$, $S_2$ and $S_3$ are renormalized as $$s_i \equiv \frac{S_i}{\sqrt{S_1^2+S_2^2+S_3^2}}, (i=1,2,3) \quad (8)$$

In the method for the precise description of the state of polarization, the Jones vector (7) should be evaluated through the renormalized Stokes vector rather than the normalized Stokes vector.

For a method for evaluating the polarization characteristics of the transmission medium, the elements of the Stokes vectors representing the incident and output states of polarization are measured, from which the Stokes vectors representing the incident and output light are developed. Then the Stokes vectors are normalized then the normalized vectors are re-normalized as shown in eq.(8). The obtained re-normalized Stokes vectors are transferred into the Jones vector representation through the expression shown in eq. (7). The relationship between the incident and output states of polarization allows us to estimate the polarization characteristics of the transmission medium in the form of the Jones matrix which conserves the geometrical symmetry.

In this method for evaluating the polarization characteristics of the transmission medium, measurement of the polarization dependent losses must be made independently of the Jones matrix measurements described above. The confirmation that the polarization dependent losses are negligible ensures the accuracy of the matrix evaluation.

This invention provides for apparatii for both evaluating the state of polarization of light and for evaluating the polarization characteristics of an optical transmission medium. The apparatus for evaluating the state of polarization of light consists of:

a means where the Jones vector describing the light is normalized in accordance with equation (2), so that the norm of the vector $\Psi$ becomes unity and a means where the Stokes vector, comprising four elements each representing a different intensity measurement of the light, is normalized to form $S_1=Q/I$, $S_2=U/I$ and $S_3=V/I$, and where the normal of this vector represents the degree of polarization of the measured light.

The apparatus for evaluating the polarization characteristics of an optical transmission medium, consists of, in addition to the above,

- a means where the normalized Stokes vector is renormalized to form elements $s_1$, $s_2$, and $s_3$ in accordance with equation (8),
- a means for evaluating the state of polarization in accordance with equation (7) utilizing the renormalized Stokes elements,
- a means for generating and launching light, which is sequentially constrained to at least three different states of polarization, into the optical transmission medium,
- a means for measuring the different intensities corresponding to the elements of the Stokes vector,
- a means where the Jones matrix representing the polarization characteristics of the optical transmission medium is calculated from the normalized or renormalized Stokes elements and the Jones vectors representing the different states of polarized light launched into the optical transmission medium, and where the elements of the Jones matrix are calculated to conserve geometrical symmetry with the matrix having the unimodular unitary form.

For the application of the above methods to the measurent of polarization mode dispersion, the present invention consists of the following procedures:

Measuring the output states of polarization after transmission through the optical medium. These output states correspond to the launched states of polarization and the number of the launched states of polarization must be at least three.

The measured output states of polarization from the optical transmission medium are put in the form of the Stokes vectors, which are normalized as described in the Stokes vector normalization section, and then the normalized Stokes vector is renormalized in accordance with the Stokes vector renormalization method described above.

Utilizing the polarization characteristics evaluation section as described before, Jones matrices at two optical angular frequencies with finite difference $\Delta\omega$; $\omega$ and $\omega+\Delta\omega$ are estimated. Then, by using the finite difference approximations, the characteristic hermitian matrix H defined as $H \equiv 2i\, dU/d\omega\, U+$ is estimated from the corresponding matrix $U(\omega)$ and $U(\omega+\Delta\omega)$.

The characteristic hermitian matrix estimation enables us to express the polarization dispersion vector $\Omega$ as a function of the hermite matrix. Normalization of the polarization dispersion vector provides the differential group delay.

When estimating the differential group delay time of principal states of polarization, separate measurements of the degree of polarization of light after the optical transmission medium, the polarization dependent losses and the diagonal elements of the hermitian matrix H defined as $H \equiv 2i\, dU/d\omega\, U+$ are made separately from the polarization mode dispersion measurement. The measurement accuracy of the differential group delay time estimation is confirmed when the following conditions are met: Measured degree of polarization is less than the unity; polarization dependent losses are negligible; and the ratio of the imaginary and the real parts of the diagonal elements of the hermitian matrix is less than the unity.

In the application of the methods to the measurent of polarization mode dispersion, the output light is split into four and measurements of the polarization characteristics corresponding to each of the Stokes parameters, I, Q, U, V are made using analyzers and quarter wave plates. Then from these measured quantifies the normalized Stokes parameters are obtained as $S_1=Q/I$, $S_2=U/I$ and $S_3=V/I$.

The apparatus used for the application to measuring polarization mode dispersion consists of the polarization input means where the incident optical beam is controlled in order to launch the three different states of polarization into the optical transmission medium; the output state of polarization evaluation means where the corresponding three output states of polarization are estimated from which the Stokes vectors are formed as shown in eq.(3), and the Stokes vector normalization means where the estimated Stokes vector is normalized as $S_1=Q/I$, $S_2=U/I$ and $S_3=V/I$ so as to provide for the norm of the normalized Stokes vector to coincide with the degree of polarization of the measured light.

In this application for measuring the polarization mode dispersion which utilizes normalized Stokes parameters, the normalized Stokes parameters $S_1$, $S_2$ and $S_3$ are renormalized using the norm of the normalized vectors as $s_i/(S_1^2+S_2^2+S_3^2)^{1/2}$, $(i=1, 2, 3)$ In this method the normalized Jones vector is represented as shown in eq.(9)

$$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2+i S_3 \end{bmatrix} \quad (9)$$

then the Stokes parameter measurements and its normalizing and renormalizing procedure provides the above estimates of the normalized Jones.

In this application to the method for polarization mode dispersion measurement, the three incident states of polarization A, B and C represented as $$\xi_A = \begin{bmatrix} \xi_A^1 \\ \xi_A^2 \end{bmatrix}, \xi_B = \begin{bmatrix} \xi_B^1 \\ \xi_B^2 \end{bmatrix}, \xi_C = \begin{bmatrix} \xi_C^1 \\ \xi_C^2 \end{bmatrix} \quad (10)$$

and the normalized Stokes vectors obtained from the measurements of the output states of polarization corresponding to the incident states of polarization, A, B and C as $$S_A = \begin{bmatrix} S_1^A \\ S_2^A \\ S_3^A \end{bmatrix}, S_B = \begin{bmatrix} S_1^B \\ S_2^B \\ S_3^B \end{bmatrix}, S_C = \begin{bmatrix} S_1^C \\ S_2^C \\ S_3^C \end{bmatrix} \quad (11)$$

which when renormalized to form the renormalized Stokes vectors allow the following relationships to the normalized Jones vector elements to be formed:

$$\frac{1+s_1^A}{\sqrt{2(1+s_1^A)}} \exp(i\gamma_A) = u_1 \xi_1^A + u_2 \xi_2^A, \quad (12a)$$

$$\frac{1+s_1^B}{\sqrt{2(1+s_1^B)}} \exp(i\gamma_B) = u_1 \xi_1^B + u_2 \xi_2^B, \quad (12b)$$

$$\frac{s_2^A + i s_3^A}{\sqrt{2(1+s_1^A)}} \exp(i\gamma_A) = u_1^* \xi_2^A - u_2^* \xi_1^A \quad (12c)$$

and $$\frac{s_2^B + i s_3^B}{\sqrt{2(1+s_1^B)}} \exp(i\gamma_B) = u_1^* \xi_2^B - u_2^* \xi_1^B \qquad (12d)$$

Combining the above relationships allows the Jones matrix elements to be represented in terms of the renormalized Stokes parameters, which includes an undermined parameter $\gamma A$ as $$U = \begin{bmatrix} u_1 & u_2 \\ -u_2^* & u_1^* \end{bmatrix} = \frac{1}{\sqrt{|m_1|^2 + |m_2|^2}} \begin{bmatrix} m_1(\gamma_A) & m_2(\gamma_A) \\ -m_2^*(\gamma_A) & m_1^*(\gamma_A) \end{bmatrix} \qquad (13)$$

Then in order to determine the parameter $\gamma_A$, the relationship derived from the response to the input polarization state C is used where, $$\frac{\exp(i\gamma_C)}{\sqrt{2(1+s_1^C)}} \begin{bmatrix} 1+S_1^C \\ S_2^C + i S_3^C \end{bmatrix} = \frac{1}{\sqrt{2(|m_1|^2+|m_2|^2)}} \begin{bmatrix} m_1 + m_2 \\ m_1^* - m_2^* \end{bmatrix} \qquad (14)$$

from which the parameters $\gamma_a$ and $\gamma_c$ can be determined. Thus all of the matrix elements are determined and the matrix satisfies the unimodular unitarity conditions.

In this application to the method of polarization mode dispersion measurement, the magnitude of the ratio $\eta$ of the imaginary and real part of the diagonal elements of the hermitian matrix H. generated using the Jones matrix of the medium as $$H = 2i \frac{dU}{d\omega} U^+,$$

needs to be less than a suitable threshold. This ratio must be chosen to satisfy the condition $0 \leq \eta \leq 1$. This ratio can then be used to determine the suitable frequency step-size discussed above.

This invention further provides apparatii for measuring polarization mode dispersion, consisting of:

a means for generating polarized light and launching this into an optical transmission medium, and sequentially changing to other, and at least three, states of polarization, a means for measuring the intensities of the light emerging from the optical transmission medium, in terms of the Stokes elements, and repeating these measurements for each of the different states of polarized light launched into the medium, and for different optical angular frequencies $\omega$ and $\omega+\Delta\omega$, a means for estimating the state of polarization of the emerging light for each of the launched states of polarization, in the form of Stokes vectors as shown in equation(3), and for normalizaing and renormalizing these vectors, means for calculating the Jones matrices describing the polarization characteristics of ahe optical transmission medium at the two optical angular frequencies $\omega$ and $\omega+\Delta\omega$ in the form of unimodular unitary matrices, and where the Jones matrices elements are calculated so as to conserve the geommetrical symmetry of the matrices by the use of renormalized Stokes vectors;

a means for calculating the Jones matrices $U\omega$ and $U(\omega+\Delta\omega)$ describing the polarization characteristics of the optical transmission medium at the two optical angular frequencies $\omega$ and $\omega+\Delta\omega$ in the form of a unimodular unitary matrices, and where the Jones matrices elements are calculated so as to conserve the geometrical symmetry of the matrices by the use of renormalized Stokes vectors, a means for estimating the polarization mode dispersion, by applying numerical estimation techniques to obtain the hermitian matrix H, where $$H = 2i \frac{dU}{d\omega} U^+,$$

from the two Jones matrices $U(\omega)$ and $U(\omega+\Delta\omega)$ by the use of finite difference approximation methods, a means for calculating the polarization dispersion vector $\Omega$ being a function of the matrix H, and then of calculating the norm of this vector $\Omega$ to generate the differential group delay times of the principal states of polarization.

An additional embodiment of this apparatus provides for the light emerging from the optical transmission medium to be divided into four portions, each of which is passed through optical elements to separate intensity measurement systems, and the optical elements configured such that each of the four Stokes elements can be simultaneously obtained for each input polarization mode, and for the Stokes vector to be constructed from these four measurements and normalized such that $S_1=Q/I$, $S_2=U/I$ and $S_3$ V/I, thus providing the normalized Stokes vector.

A further additional embodiment of this apparatus provides a means for renormalizing the Stokes elements as $$Si = \frac{S_i}{\sqrt{S_1^2 + S_2^2 + S_3^2}}, (i = 1, 2, 3)$$

and using these in the calculation of the Jones matrices.

A yet further additional embodiment of this apparatus provides a means for adjusting and controlling the optical angular frequency interval, $\Delta\omega$ used in defining the two frequencies $\omega$ and $\omega+\Delta\omega$ at which the two Jones matrices $U(\omega)$ and $U(\omega+U\omega)$ are calculated. The ratio between the imaginary and real parts of the diagonal elements of the matrix H is calculated, and the value of $\Delta\omega$ adjusted until $\rho$ satisfies the condition of $0 \leq |\rho| \leq |$.

Since the normalized Stokes vector elements may be expressed as a function of the Jones vector as shown in eq.(39), correspondingly it should be possible to express the Jones vector elements as a function of the normalized Stokes vector. However such an expression has not previously been developed. In order to study the representation of the Jones vector as a function of the normalized Stokes parameters, eq.(39) has been solved with respect to the Jones vector from which the following two representations are obtained $$\xi' = \begin{bmatrix} \xi_1' \\ \xi_2' \end{bmatrix} = \frac{\exp(i\gamma)}{\sqrt{2(1-S_1)}} \begin{bmatrix} 1-S_1 \\ S_2 + i S_3 \end{bmatrix} \qquad (42)$$

and $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + i S_3 \end{bmatrix} \qquad (43)$$

Direct insertion of these results into eq.(39) confirms that both these solutions satisfy the relationship between the Jones and Stokes vector, therefore further analysis is required to determine which solution corresponds to the conventional Jones vector representation of the polarized light. The results of considering a number of polarization states in terms of the Stokes Vector, Conventional Jones Vector and equations 42 and 43 are summarized in Table 2.

the assumption that the influences of the polarization dependent losses are negligible. Then three incident states of polarization are considered. These states of polarization, namely A, B and C are represented within the framework of the Jones analysis as follows:

TABLE 2

| State of Polarization | Stokes vector | Conventional Jones vector | eq. (42) | eq. (43) |
|---|---|---|---|---|
| horizontal linear polarization | (1, 0, 0) | (1, 0) | (0, 1) | (1, 0) |
| vertical linear polarization | (−1, 0, 0) | (0, 1) | (1, 0) | (0, 1) |
| linear polarization by azimuth angle + 45 deg. | (0, 1, 0) | $1/\sqrt{2}\,(1, 1)$ | $1/\sqrt{2}\,(1, 1)$ | $1/\sqrt{2}\,(1, 1)$ |
| linear polarization by azimuth angle − 45 deg. | (0, −1, 0) | $1/\sqrt{2}\,(1, -1)$ | $1/\sqrt{2}\,(1, -1)$ | $1/\sqrt{2}\,(1, -1)$ |
| right hand circular polarization | (0, 0, 1) | $1/\sqrt{2}\,(1, i)$ | $1/\sqrt{2}\,(1, i)$ | $1/\sqrt{2}\,(1, i)$ |
| left hand circular polarization | (0, 0, −1) | $1/\sqrt{2}\,(1, -i)$ | $1/\sqrt{2}\,(1, -i)$ | $1/\sqrt{2}\,(1, -i)$ |

The solutions of eq.(42) and eq.(43) have regularly limits (0, 1) and (1, 0) respectively in the singular state of polarization limit and the results are included in the above table. Here the appropriate value of the absolute phase constant y is used in order to summarize the results. The table clearly shows that eq.(43) corresponds perfectly to the conventional use of Jones vectors. In the above discussions, the explicit expression of the Jones vector is obtained as a function of the normalized Stokes parameters.

Also in the above, the relationship shown in eq.(37) is implicitly assumed indicating that eq.(43) is not applicable for partially polarized light. Thus in order to use Jones vectors constructed from normalized Stokes parameters, a measure of the degree of polarization of light is required. In cases where the measured light is almost perfectly polarized, eq.(43) is applicable to constructing the Jones vector, but using the renormalized Stokes vectors instead of the normalized Stokes vectors. This invention also provides an approximation method to construct Jones vectors for the partially polarized light. In cases where the degree of polarization is less than unity but still sufficiently large, use can be made of the renormalized Stokes parameters to construct the Jones vector using eq.(43).

The Jones matrices are of the unimodular unitary matrix form shown in eq.(21) for cases where the polarization dependent loss as in the optical transmission medium are zero. However, in practice, when using real media, polarization losses in the transmission medium cannot be neglected. Where the influences of the polarization dependent losses are finite but negligible, it is useful to use the unitary matrix representation of the medium to analyze the polarization effects. But in the case of the polarization mode dispersion measurements which use the Jones matrix eigenanalysis approach, violation of the matrix unitarity criteria requires the introduction of the exponential approximation, an approach which has no relevance to the principal states of polarization. To address these limitations, a symmetry conserving unitary matrix construction procedure has been developed and is shown as follows.

Initially, it is necessary to measure the polarization dependent losses as in the optical transmission medium to validate $$\xi_A = \begin{bmatrix} \xi_A^1 \\ \xi_A^2 \end{bmatrix}, \xi_B = \begin{bmatrix} \xi_B^1 \\ \xi_B^2 \end{bmatrix}, \xi_C = \begin{bmatrix} \xi_C^1 \\ \xi_C^2 \end{bmatrix} \tag{44}$$

Then the output states of polarization corresponding to the incident states of polarization A, B and C are as represented by the renormalized Stokes vectors as $$s_A = \begin{bmatrix} s_1^A \\ s_2^A \\ s_3^A \end{bmatrix}, s_B = \begin{bmatrix} s_1^B \\ s_2^B \\ s_3^B \end{bmatrix}, s_C = \begin{bmatrix} s_1^C \\ s_2^C \\ s_3^C \end{bmatrix} \tag{45}$$

Combining the Jones matrix (22) and the relationship between the Jones vector with the renormalized Stokes vector shown in eq.(43), the following derived relationships are $$\frac{1 + s_1^A}{\sqrt{2(1 + s_1^A)}} \exp(i\gamma_A) = u_1 \xi_1^A + u_2 \xi_2^A \tag{46.1}$$

$$\frac{1 + s_1^B}{\sqrt{2(1 + s_1^B)}} \exp(i\gamma_B) = u_1 \xi_1^B + u_2 \xi_2^B \tag{46.2}$$

$$\frac{s_2^A + i s_3^A}{\sqrt{2(1 + s_1^A)}} \exp(i\gamma_A) = u_1^* \xi_2^A - u_2^* \xi_1^A \tag{46.3}$$

and $$\frac{s_2^B + i s_3^B}{\sqrt{2(1 + s_1^B)}} \exp(i\gamma_B) = u_1^* \xi_2^B - u_2^* \xi_1^B \tag{46.4}$$

Each of the above four equations may be partitioned into the real and imaginary parts leading to 8 separate equations. However they are subject to the following implicit matrix and vector constraints:

$$|u_1|^2 + |u_2|^2 = 1 \tag{47}$$

$$|\xi_1^A|^2 + |\xi_2^A|^2 = 1 \tag{48}$$

$$|\xi_1^B|^2 + |\xi_2^B|^2 = 1 \tag{49}$$

hence the degrees of freedom of these equations decreases and becomes 5. Since the number of the variables is 6; being the real and imaginary parts of $u_1$ and $u_2$, and two absolute phase factors $\gamma_A$ and $\gamma_B$, the indefinite variables are not determinable from the set of equations (46).

However, for the reasons discussed above, one can construct the unitary matrix by introducing a variable $\gamma$ where $$\gamma = -\gamma_A - \gamma_B \tag{50}$$

which leads to the following, where $\gamma_A$ is the only undetermined variable.

$$U = \begin{bmatrix} u_1 & u_2 \\ -u_2^* & u_1^* \end{bmatrix} = \frac{1}{\sqrt{|m_1|^2 + |m_2|^2}} \begin{bmatrix} m_1(\gamma_A) & m_2(\gamma_A) \\ -m_2^*(\gamma_A) & m_1^*(\gamma_A) \end{bmatrix} \tag{51}$$

Then in order to determine the remaining parameter $\gamma_A$, we use relationship derived by the response to polarization C is used.

$$\frac{\exp(i\gamma_C)}{\sqrt{2(1+s_1^C)}} \begin{bmatrix} 1+s_1^C \\ s_2^C + is_3^C \end{bmatrix} = \frac{1}{\sqrt{2(|m_1|^2 + |m_2|^2)}} \begin{bmatrix} m_1 + m_2 \\ m_1^* - m_2^* \end{bmatrix} \tag{52}$$

Mathematically the number of equations has been increased in order to give equality between the number of the variables and the number of equations.

The above relationship of eq.(52) enables us to determine the parameters $\gamma_A$ and $\gamma_C$ uniquely. Consequently all of the matrix elements are determined and the obtained matrix satisfies the unimodular unitarity conditions. From the expression shown in eq.(5 1), the obtained matrix is guaranteed to be an element of the unimodular unitary matrix.

As mentioned in the preceding discussions, first of all, it is necessary to measure the polarization dependent loss of the optical transmission medium to confirm the validity of the assumption that the influences of the polarization dependent loss are negligible. Furthermore it is also necessary to measure the degree of polarization of the output light. According to the theory of the principal states of polarization, if the spectrum width of the light is narrow enough to satisfy the first order approximation, the output light will never depolarize. After confirming the above two conditions, according to the scheme described above, the Jones matrix of the optical transmission medium can be evaluated in the form of a unitary matrix.

Next using spinor to vector transformations and applying these to the theory of the principal states of polarization, a representation of the polarization dispersion vector elements can be developed. In these discussions, the Jones vector is considered to include an absolute phase factor and vector $\Psi$ is used instead of $\xi$. Then the relation between the input and output state of polarization is represented as $$\Psi_{out}(\omega) = U(\omega)\Psi_{in} \tag{53}$$

$$\Psi_{in} = U^+(\omega)\Psi_{out}(\omega) \tag{54}$$

where + represents the hermite conjugate of the matrix. According to the discussion by Poole and Wagner (ref.[6]), it can be assumed that incident state of polarization is fixed and independent of the angular frequency. Using the relationship of eq.(54) to develop both sides of equation(53) results in the following characteristic equation(ref.[34]).

$$i\frac{d\psi_{out}}{d\omega} = \frac{1}{2}H(\omega)\psi_{out} \tag{55}$$

here H is defined as $$H(\omega) = 2i\frac{dU}{d\omega}U^+ \tag{56}$$

and it is easily proved the matrix is hermitian. Inserting eq.(22), leads to the explicit expression of the matrix $$H(\omega) = \begin{bmatrix} h_1(\omega) & h_2(\omega) \\ h_2^*(\omega) & -h_1(\omega) \end{bmatrix} \tag{57}$$

where the matrix elements are $$h_1 \equiv \frac{2}{i}\left(u_1\frac{du_1^*}{d\omega} + u_2\frac{du_2^*}{d\omega}\right) \tag{58.a}$$

and $$h_2 \equiv \frac{2}{i}\left(u_2\frac{du_1}{d\omega} - u_1\frac{du_2}{d\omega}\right) \tag{58.b}$$

Here it is easily proved that the $h_1$ is a real function. In order to find a unique solution for eq.(55), the following eigenvalue equation is considered, being analogous to the steady state equations appearing in the quantum mechanics.

$$H\xi = \epsilon\xi \tag{59}$$

a solution to which is obtained analytically as follows. The eigenvalues are $$\varepsilon_+ = \sqrt{\left|\frac{du_1}{d\omega}\right|^2 + \left|\frac{du_2}{d\omega}\right|^2} \tag{60}$$

and $$\varepsilon_- = -\sqrt{\left|\frac{du_1}{d\omega}\right|^2 + \left|\frac{du_2}{d\omega}\right|^2} \tag{61}$$

and the corresponding eigenvectors are $$\xi_+ = \begin{bmatrix} h_1 + 2\varepsilon_+ \\ h_2^* \end{bmatrix}, \quad \text{and} \quad \xi_- = \begin{bmatrix} h_1 + 2\varepsilon_- \\ h_2^* \end{bmatrix} \tag{62}$$

Then by using eq.(30) it is easily shown that $$\frac{d\varepsilon_\pm}{d\omega} = \frac{dh_1}{d\omega} = \frac{dh_2}{d\omega} = 0 \tag{63}$$

which allows the following conditions to be derived $$\frac{d\xi_+}{d\omega} = \frac{d\xi_-}{d\omega} = 0 \tag{64}$$

These results indicate that the eigenvector(62) satisfies the condition of the output principal states of polarization and that the relationship shown in eq.(30) is necessary to realize the first order approximation. Furthermore subtraction of the above two eigenvalue coincides with the DGD time of the PSPs as shown in eq.(31):

$$|\varepsilon_+ - \varepsilon_-| = 2\sqrt{\left|\frac{du_1}{d\omega}\right|^2 + \left|\frac{du_2}{d\omega}\right|^2} = \Delta\tau \quad (65)$$

The physical meaning of this solution will now be discussed. From the above, the state of polarization as a special solution of the eq.(55) may be written in the following form $$\psi_+(\omega) = \xi_+ \exp\left[-\frac{i}{2}\Delta\phi(\omega)\right] \text{ and } \psi_-(\omega) = \xi_- \exp\left[\frac{i}{2}\Delta\phi(\omega)\right] \quad (66)$$

where $\Delta\Phi$ is the phase factor which satisfies the condition $$\frac{d\Delta\phi(\omega)}{d\omega} = 2\sqrt{\left|\frac{du_1}{d\omega}\right|^2 + \left|\frac{du_1}{d\omega}\right|^2} = \Delta\tau(\omega) \quad (67)$$

It is understood that the above solutions include the same physical meaning as the theory of principal states of polarization put forward by Poole and Wagner. Then in the following discussions, the eq.(55) is adopted as the basic equation to describe the frequency dependence of the state of polarization and consider the relationship to the vector equation shown in eq.(32).

For the convenience of discussion, the relationship between the normalized Stokes parameter and the corresponding Jones vector is rewritten as $S=\Theta(\Psi\sigma\omega^+)$, where $\sigma$ is the Pauli matrices:

$$\sigma = \begin{bmatrix} \sigma_1 \\ \sigma_2 \\ \sigma_3 \end{bmatrix}, \sigma_1 = \begin{bmatrix} 0 & 1 \\ 1 & 0 \end{bmatrix}, \sigma_2 = \begin{bmatrix} 0 & -i \\ i & 0 \end{bmatrix}, \sigma_3 = \begin{bmatrix} 1 & 0 \\ 0 & -1 \end{bmatrix} \quad (68)$$

and $\Theta$ is a 3 dimensional coordinate transformation matrix $$\Theta = \begin{bmatrix} 0 & 0 & 1 \\ 1 & 0 & 0 \\ 0 & 1 & 0 \end{bmatrix} \quad (69)$$

Applying the vector to spinor transformation as shown above, eq.(55) can be transformed to the vector field equation providing the same results as eq.(32) (ref.[20]). In this transformation, both the characteristic hermite matrix H and the polarization dispersion vector $\Omega$ play important roles and cam be used to derive the elements of the polarization dispersion vector as follows $$\Omega = \begin{bmatrix} h_1 \\ \text{Im}(h_2) \\ \text{Re}(h_2) \end{bmatrix} \quad (70)$$

Then the polarization dispersion vector may be determined experimentally through the Jones matrix estimation using eq.(56). Differential group delay time of the principal states of polarization $\Delta\tau$ is estimated as the norm of the polarization dispersion vector using the following relationship $$\Delta\tau = |\Omega| = \sqrt{h_1^2 + |h_2|^2} = 2\sqrt{\left|\frac{du_1}{d\omega}\right|^2 + \left|\frac{du_1}{d\omega}\right|^2} \quad (71)$$

In practice in order to estimate the characteristic matrix H from the Jones matrix, the following finite differential approximation is applied $$\frac{du_i}{d\omega} = \frac{u_i(\omega + \Delta\omega) - u_i(\omega)}{\Delta\omega}, (i = 1, 2) \quad (72)$$

By choosing $\Delta\omega$ to be sufficiently small in order to satisfy the above approximation, the estimated value of $h_1$ can be expected to be a real number. However in the practical experiments, unavoidable measurement errors will give rise to a finite imaginary part of $h_1$ and the ratio of the imaginary and real part of the matrix elements becomes $$\left|\frac{\text{Im}[h_1]}{\text{Re}[h_1]}\right| \ll 1 \quad 73)$$

when $\Delta\omega$ is sufficiently small. In order to estimate a suitable size for $\Delta\omega$, a threshold value $\rho$ satisfying the following condition is considered $$\left|\frac{\text{Im}[h_1]}{\text{Re}[h_1]}\right| \leq \eta \ll 1 \quad (74)$$

A suitable choice of the threshold value enables the measurement accuracy of the measurement to be determined. By estimating the left hand side of eq.(73) it can be confirmed whether the measurements can be made using a first order approximation approach and at only two wavelengths.

Stokes vector trajectory observations are applied to confirm the suitability of the stepsize $\Delta\omega$. If the stepsize is larger than the suitable stepsize discussed above, the trajectory deviates from the ideal circle on the Poincare sphere. In order to determine any circle on the sphere surface uniquely, it is necessary to observe at least three points. This requires the use of at least three frequencies to determine the frequency step-size; $\omega_o$, $\omega_O+\Delta\omega$ and $\omega_o+2\Delta\omega$. However, based on the above discussions, the applicability of the measurements is limited in the following manner. First consider the case where the wavelength dependence of the Jones matrix elements $u_i$ (i=1, 2, 3) is as shown in FIG. 4 and the derivative value of the $u_i$ with respect to $\lambda$, at $\lambda_o$=1550 nm is required. According to the above discussions, for the condition where the wavelength accuracy of the tunable laser is $\Delta\lambda$=0.6 nm, the Stokes vector trajectory observations will lead to the choice of the optimum stepsize with an accuracy of $2\Delta\lambda$=1.2 nm. As seen in FIG. 4, the gradient obtained by such roughly approximated procedure with $2\Delta\lambda$=1.2 nm is apparently different from the true value. On the other hand, since only two points are necessary to evaluate the left hand side of the eq.(74a), more precise optimum stepsize estimation is possible with an accuracy of $\Delta\lambda$=0.6 nm.

Thus estimation of the eq.(74) enables the use of a wider optimization limit than permitted by conventional methods while retaining high measurement accuracy and determines the optimum wavelength (or equivalent frequency) stepsize.

Practical Jones matrix measurements will now be considered. Although the original method to measure the Jones matrices proposed by Jones, respects in principle the symmetry properties, his method is very sensitive to the unavoidable experimental errors and the influences of the existence of the polarization dependent losses which violate the symmetry properties. In principle, if the degree of polarization through the optical transmission medium is sufficiently large and polarization dependent losses of the medium are negligible, the unitary matrix expression of the obtained Jones matrix is available for the polarization property analysis of the transmission medium.

With respect to the polarization mode dispersion measurement, the concept of the principal state of polarization is based on the unimodular unitary property of the Jones matrix and it is now regarded that this concept plays a fundamental role in polarization mode dispersion analysis. Thus in order to apply the concept of principal state of polarization to actual experiments, an experimental method to measure the Jones matrix which preserves the symmetry property of the matrix in each step of the experiment is required. The matrix construction method is shown in the following discussions.

It is well known that the Jones analysis and Mueller analysis are both useful in the study of the polarization optics(reference[18]). In the Jones analysis, the state of polarization (SOP) is represented by a 2 dimensional complex vector, called Jones vector and the birefringence property of the transmission medium is described by a complex 2×2 matrix, called the Jones matrix. On the other hand, in the Mueller analysis, the state of polarization (SOP) is represented essentially by a 3 dimensional real vector, called normalized Stokes vector and the birefringence properly of the transmission medium is described by a complex 3×3 matrix, called Mueller matrix(reference[18]). In 1972, Takenaka studied the geometrical relationships of these two linear transformations and the class of those matrices which correspond to the rotational group in the 3 dimensional Euclidian space which leads to the treatment of Jones vectors in the spinorial manner and Stokes vectors in the vectorial manner.

It is known that where the optical light is perfectly polarized, the normalized Jones vector $$\xi = \begin{bmatrix} \xi_1 \\ \xi_2 \end{bmatrix} \qquad (75)$$

corresponds to the normalized Stokes vector in the following manner:

$$S = \begin{bmatrix} S_1 \\ S_2 \\ S_3 \end{bmatrix} = \begin{bmatrix} |\xi_1|^2 - |\xi_2|^2 \\ 2\mathrm{Re}(\xi_1\xi_2^*) \\ -2\mathrm{Im}(\xi_1\xi_2^*) \end{bmatrix} \qquad (76)$$

where Re[z] and Im[z] represents the real and imaginary part of z, and , is the normalized complex amplitude of the electric field. The Stokes vector elements have the dimensions of the optical power and are measurable quantities. On the other hand the elements of the normalized Jones vector have the dimensions of the electric field and cannot be measured directly. In order to obtain the Jones vector by measurements, it is necessary to write the Jones vector elements in terms of measurable quantities. Solving the eq.(76) with respect to $\xi$, the Jones vector can be rewritten as a function of the measurable quantities of the Stokes elements.

$$\xi' = \begin{bmatrix} \xi_1' \\ \xi_2' \end{bmatrix} = \frac{\exp(i\gamma)}{\sqrt{2(1+S_1)}} \begin{bmatrix} 1+S_1 \\ S_2 + i S_3 \end{bmatrix} \qquad (77)$$

$$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + i S_3 \end{bmatrix} \qquad (78)$$

where $\gamma$ is the absolute phase constant. According to the conventional manner for describing the states of polarization, direct insertion of the corresponding Stokes parameters leads us to the fact that eq.(78) is appropriate choice rather than eq.(77). Thus using the following procedure, it is possible to construct the Jones matrix that conserves unitarity symmetry.

Consider three incident states of polarization. These states of polarization, namely A, B and C are represented within the framework of the Jones analysis as shown in eq.(10). Expressing the Jones matrix of the optical transmission medium as a unimodular unitary matrix, and the output states of polarization by renormalized Stokes vectors corresponding to the incident states of polarization A, B and C, the following relationships can be derived:

$$\frac{1+s_1^A}{\sqrt{2(1+s_1^A)}}\exp(i\gamma_A) = u_1\xi_1^A + u_2\xi_2^A \qquad (46.1)$$

$$\frac{1+s_1^B}{\sqrt{2(1+s_1^B)}}\exp(i\gamma_B) = u_1\xi_1^B + u_2\xi_2^B \qquad (46.2)$$

$$\frac{s_2^A + is_3^A}{\sqrt{2(1+s_1^A)}}\exp(i\gamma_A) = u_1^*\xi_2^A - u_2^*\xi_1^A \qquad (46.3)$$

and $$\frac{s_2^B + is_3^B}{\sqrt{2(1+s_1^B)}}\exp(i\gamma_B) = u_1^*\xi_2^B - u_2^*\xi_1^B \qquad (46.4)$$

Each of the above four equations may be partitioned into real and imaginary parts, resulting in 8 separate equalities. However they are subject to the following implicit matrix and vector constraints $$|u_1|^2 + |u_2|^2 = 1 \qquad (47)$$

$$|\xi_1^A|^2 + |\xi_2^A|^2 = 1 \qquad (48)$$

$$|\xi_1^B|^2 + |\xi_2^B|^2 = 1 \qquad (49)$$

hence the degrees of freedom of these equations decreases to 5. Since the number of the variables is 6, being the real and imaginary parts of $u_1$ and $u_2$, and two absolute phase factors $\gamma_A$ and $\gamma_B$, the indefinite variables are not determinable from these equations. However, for the reasons discussed above, one can construct the unitary matrix by introducing a variable $\gamma$ where $$\gamma = -\gamma_A - \gamma_B \qquad (50)$$

which leads to the result shown in equation(51) where $\gamma_A$ is the only undetermined variable. Then in order to determine the remaining parameter $\gamma_A$, the relationship derived by the response to polarization C is used. Thus the number of equations has been increased to give equality between the number of the variables and the number of equations. Hence all of the matrix elements are determinable and the matrix so obtained satisfies the unimodular unitarity condition.

Before conducting the experiments implied by the above discussions, the polarization dependent losses of the optical transmission medium are measured to confirm the validity of the assumption that the influences of the polarization dependent losses are negligible, and thus that an accurate matrix estimation is possible.

The above matrix measurements are made at two angular frequencies; $\omega_o$ and $\omega_o+\Delta w$ where $\Delta\omega$ is the frequency stepsize discussed earlier, and from which $dU/d\omega$ can be evaluated using finite difference approximation. Since the obtained Jones matrices $U(\omega_o)$ and $U(\omega_o+\Delta w)$ are both unitary, then the appropriate choice of the $\Delta\omega$ ensures the hermiticity of the estimated matrix H, where H=2i dU/d $\omega$ $U^+$. The explicit form of this matrix is shown in eq.(57). The matrix elements are closely related to the polarization dispersion vector shown in reference [22] and [29]. If the elements of the polarization dispersion vector are as $$\Omega = \begin{vmatrix} \Omega_1 \\ \Omega_2 \\ \Omega_3 \end{vmatrix}$$

where $h=Q\;\Omega_1$, $h_2=\Omega_2-i\Omega_3$, then the polarization dispersion vector may be written as a function of the Jones matrix elements, Thus it is shown that using Jones matrix measurements at two frequencies enable the polarization dispersion vector to be evaluated and thus allows the differential group delay time $\Delta\tau$ to be estimated from the norm of the vector, where $$\Delta\tau=|\Omega|=(h_1^2+h_2^2)^{1/2}$$

In this approach, as discussed above, the hermiticity of the matrix H is ensured when the frequency step-size is chosen to satisfy the first order approximation requirements. If $\Delta\omega$ is larger than optimum, higher order effects will result in a finite imaginary part of $h_1$. Therefore that quantity which is defined as the magnitude of the ratio of the imaginary and real parts of $h_1$, provides a measure for use in estimating the optimum step-size. A variable $\rho$ is introduced which satisfies the condition: $|Im(h1)/Re(h1)| \leq \rho \leq 1$ is used in determining this optimum frequency stepsize.

The present invention provides a method wherein the Jones vector, which represents the state of polarization of light, can be expressed in terms of the normalized or renormalized Stokes elements, and a method by which the Jones matrix, which describes the polarization properties of the optical transmission medium, can be constructed from these Jones vectors while conserving the unimodular unitary symmetry. Therefore the evaluation of the state of polarization of light and polarization characteristics of the optical transmission medium, which is difficult within the framework of the traditional Jones analysis, can be accurately performed using Jones matrices in a manner consistent with the Mueler's analysis.

In addition, by introducing the renormalized Stokes vector, which is obtained through the normalization of the conventional normalized Stokes vector, it is possible to evaluate the state of polarization of light and polarization characteristics of the optical transmission medium in the presence of unavoidable measurement errors, small polarization dependent losses and small deviations from perfect polarization conditions.

Furthermore, the present invention provides these approaches to the evaluation of the state of polarization of light and polarization characteristics of the optical transmission medium which are applicable to various industrial optical fields using optical polarization additional to the more usual field of the optical communications.

Moreover, this invention has developed a clear relation between the polarization dispersion vector $\Omega$ and the characteristic hermitian matrix H defined using the Jones matrix U as H=2i dU/d$\omega$ $U^+$. Consequently, the polarization dispersion vector elements are explicitly represented as a function of the hermite matrix elements and therefore the calculation of the norm of the vector enables the differential group delay times of the principal states of polarization to be estimated. This invention has made it possible to represent the Jones vector, which represents the state of polarization of light, in terms of the Stokes elements which are measurable quantities. Furthermore this invention shows that the characteristic hermitian matrix H plays important role when describing the frequency dependence of the output Jones vector, thus making it possible to construct a novel polarization mode dispersion measurement apparatus.

Furthermore, this invention introduces the concept of the renormalized Stokes vector that is obtained by normalizing the normalized Stokes vector. By representating the Jones vector and Jones matrix in terms of the renormalized Stokes vector it is thus possible to evaluate the state of polarization of light even when it is not perfectly polarized, and to construct the Jones matrix as a unitary matrix even in the presence of unavoidable measurement errors, small polarization dependent losses, and small deviations from perfect polarization conditions.

Moreover, in this invention by introducing the characteristic hermite matrix H, defined using the Jones matrix U as H=2i dU/d$\omega$ $U^+$, the suitable frequency step-size for $\Delta\omega$ can be determined whereby a suitable and finitely small frequency interval $\Delta\omega$ is determined by estimating the ratio of the imaginary and real part of the diagonal elements of the characteristic hermitian matrix H. In this method, measurement accuracy is confirmed using a threshold criteria $\eta$; where $0 \leq \eta 1$. Then if the ratio is smaller than $\eta$, the measurements will have sufficient accuracy. The method provides for the accurate and reliable evaluation of polarization mode dispersions.

BRIEF DESCRIPTION OF THE DRAWINGS

The objects and advantages of this invention will become more apparent and be more readily appreciated from the following detailed description of the exemplary embodiments of the invention taken in conjunction with the accompanying drawings, in which.

DETAILED DESCRIPTION OF THE PREFERRED EMBODIMENT

Figure 1:
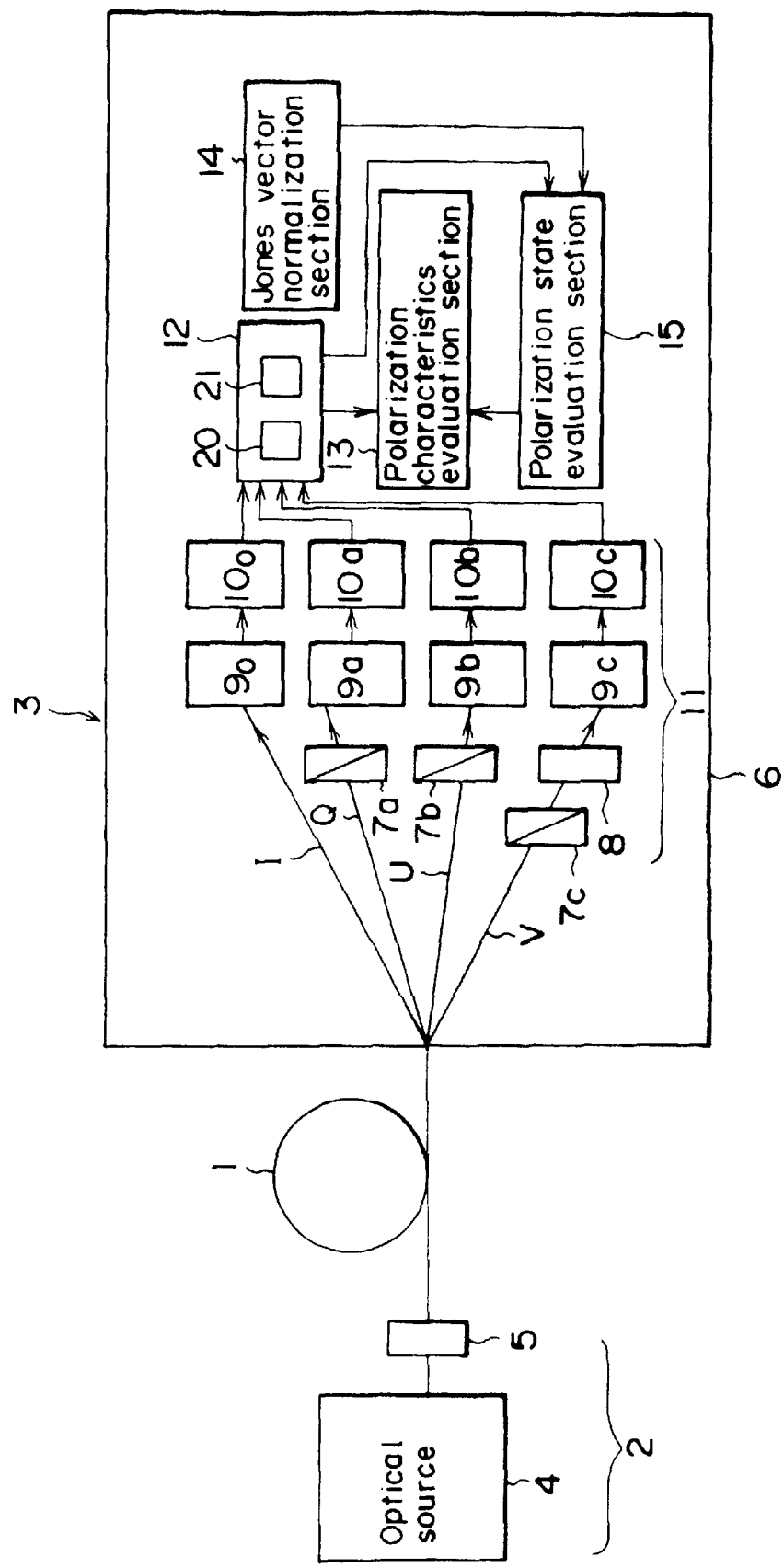
FIG. 1 is a block diagram showing the fundamental parts of an apparatus of an embodiment of the present invention which evaluates the state of polarization of light and the polarization characteristics of the optical transmission medium.

A preferred embodiment of the present invention will now be described based on the drawings. A block diagram of the preferred embodiment for the evaluation of the state of polarization and the polarization characteristics of the transmission medium of an optical transmission medium 1 is shown in FIG. 1. This apparatus has an incident-side device 2 and output-side device 3. The incident-side device 2 consists of a light source 4 and a phase compensator 5, the latter being a combination of a polarizer and wave retardation plates. The light source 4 is of narrow bandwidth and stable emission, e.g., DFB-LD. The phase compensator 5 is used to control the state of polarization of the incident light and it can generate at least 3 different states of polarization, designated A, B, and C. The optical light whose state of polarization is controlled by compensator 5, is launched into the optical transmission medium 1. The output-side device 3 consists of the output light measurement means 11 included in the main body 6, a Stokes vector normalization section 12, a polarization characteristics analysis section 13, a Jones vector normalization section 14 and a state of polarization analysis section 15.

The output light measurement means 11, consists of analyzers 7a, 7b, and 7c, a quarter wave plate 8 with no gradient of the azimuth angle, optical intensity detecting section $9_0$, $9a$, $9b$, and $9c$ and corresponding electrical interfaces $10_0$, $10a$, $10b$, and $10c$. The light transmitted through the optical transmission medium 1, being the object under study, is split into 4 portions designated I, Q, U and V.

Portion I is passed directly to the optical intensity detection section $9_0$ with its corresponding electrical interface $10_0$, which measures the overall intensity of the light emerging from the optical transmission medium. The signal representing this intensity is then passed to the Stokes vector normalization section 12, and represents the Stokes vector element 1.

Portion Q is passed to analyzer 7a, which is arranged so as to pass light to the optical intensity detection section 9a, with its corresponding electrical interface 10a, the intensity of which represents the difference in intensities between the horizontal and the vertical linearly polarized components of the light emerging from the optical transmission medium. The signal representing this intensity is then passed to the Stokes vector normalization Section 12, and represents the Stokes vector element Q.

Portion U is passed to analyzer 7b, which is arranged so as to pass light to the optical intensity detection section 9b with its corresponding electrical interface 10b, the intensity of which represents the difference in intensities between the linearly polarized components oriented at +45° and −45° of the light emerging from the optical transmission medium. The signal representing this intensity is then passed to the Stokes vector normalization section 12, and represents the Stokes vector element U.

Portion V is passed to a combination of optical elements comprising analyzer 7c and quarter wave plate 8, which are arranged so as to pass light to the optical intensity detection section 9c with its corresponding electrical interface 10c, the intensity of which represents the difference in intensities between the right and the left circularly polarized components of the light emerging from the optical transmission medium. The signal representing this intensity is then passed to the Stokes vector normalization section 12, and represents the Stokes vector element V.

Stokes vector normalization section 12 consists of the first normalization section 20 and second normalization section 21. In the first normalization section 20, Stokes vector S={I, Q, U, V} is normalized in the following manner $$S_1 = Q/I,\ S_2 = U/I,\ S_3 = V/I \tag{81}$$

The second normalization section where the normalized Stokes parameters are renormalized as $$s_i = \frac{S_i}{\sqrt{S_1^2 + S_2^2 + S_3^2}},\ (i = 1, 2, 3) \tag{82}$$

The Jones vector normalization section 14 where the complex two dimensional Jones vector $\Psi$ describing the launched polarized lights, is normalized as shown in eq.(2).

The state of polarization evaluating section 15 where the Jones vector representation of the state of polarization of the emerging light is calculated based on the following relations between the elements of a normalized Jones vector and the elements of a normalized Stokes vector.

$$S_1 = |\xi_1|^2 - |\xi_2|^2 \tag{39a}$$

$$S_2 = 2\ Rw(\xi_1 \xi_2^*) \tag{39b}$$

$$S_3 = -2\ Im(\xi_1 \xi_2^*) \tag{39c}$$

Thus, the Jones vector corresponding to the measured normalized Stokes vector is obtained in the form represented by eq.(7), which is derived from the above equations.

The polarization characteristics evaluation section 13 is where the Jones matrix of the optical transmission medium is constructed from the responses obtained from the three different incident states of polarization A, B and C launched into the medium.

The Jones matrix, as shown in eq.(20), which is subject to the unitary constraint of eq.(21), is calculated using the normalized Jones vectors describing the three input states of polarization A, B, and C as shown in Eq.(44), and using the three normalized Jones vectors calculated from the normalized Stokes vectors which describe the corresponding three emerging states of polarization.

An example of evaluating the state of polarization and polarization characteristics of an optical transmission medium using this apparatus will now be described.

In this example, the optical transmission medium consists of the two different polarization maintaining optical fibres (references [14],[15],[21]) concatenated with a finite angular misalignment. The output state of polarization and polarization characteristics of the medium are considered numerically using the methods of this invention. The output states of polarization are calculated using Mueller's approach. The study of the resultant output Jones vector, after transformation from the Stokes vector, using eq.(43) will give an important confirmation of the validity of this invention. In this example, for simplification, it is assumed that the emerging light is perfectly polarized and the polarization dependent losses of the optical transmission are zero. For cases where the light, after passing through the medium, contains a small depolarized component and/or the polarization dependent losses of the medium are not equal to zero but can still be considered negligible, the use of the renormalization procedure still permits the same approach to be followed.

It is known that in a linear birefringence medium, the linear polarization of those oscillations whose direction of polarization are parallel to and/or perpendicular to the optical axes of the medium, are conserved when passing through the medium. A well known example is that of a quarter wave plate with azimuth angle of 0 deg, which is represented in the form of the Mueller's matrix as $$Q_0 = \begin{bmatrix} 1 & 0 & 0 \\ 0 & 0 & 1 \\ 0 & -1 & 0 \end{bmatrix} \quad (83)$$

When linear polarized light of wavelength for which the retardation plate is quarter wave, whose azimuth angle is 45 deg. with respect to the principal axes of the plate, is passed through such a quarter wave plate, the output state of polarization in normalized Stokes vector form is calculated as $$S_{out1} = \begin{bmatrix} 0 \\ 0 \\ -1 \end{bmatrix} = \begin{bmatrix} 1 & 0 & 0 \\ 0 & 0 & 1 \\ 0 & -1 & 0 \end{bmatrix} \begin{bmatrix} 0 \\ 1 \\ 0 \end{bmatrix} \quad (84)$$

This indicates that the output state of polarization is right circular. The corresponding Jones matrix representation obtained using eq.(43) then becomes $$\xi_{out1} = \begin{bmatrix} \xi_1 \\ \xi_2 \end{bmatrix} = \frac{\exp(i\gamma)}{\sqrt{2(1+0)}} \begin{bmatrix} 1+0 \\ 0+1 \times i \end{bmatrix} = \frac{\exp(i\gamma)}{\sqrt{2}} \begin{bmatrix} 1 \\ i \end{bmatrix} \quad (85)$$

which is the same as the conventional Jones vector representation.

Next, a circular birefringent medium will be considered, the Mueller matrix representation of which is $$T_{\pi/4} = \begin{bmatrix} 0 & -1 & 0 \\ 1 & 0 & 0 \\ 0 & 0 & 1 \end{bmatrix} \quad (86)$$

It is known that this matrix rotates the polarization ellipse by 45 deg. In truth inserting the linear polarization with azimuth is 0 deg, the obtained output polarization vector is $$S_{out2} = \begin{bmatrix} 0 \\ 1 \\ 0 \end{bmatrix} = \begin{bmatrix} 0 & -1 & 0 \\ 1 & 0 & 0 \\ 0 & 0 & 1 \end{bmatrix} \begin{bmatrix} 1 \\ 0 \\ 0 \end{bmatrix} \quad (87)$$

The result indicates that the output state of polarization is linear polarized at an azimuth angle of 45°. The corresponding Jones matrix representation obtained from eq.(43) is $$\xi_{out2} = \begin{bmatrix} \xi_1 \\ \xi_2 \end{bmatrix} = \frac{\exp(i\gamma)}{\sqrt{2(1+0)}} \begin{bmatrix} 1+0 \\ 1+0 \times i \end{bmatrix} = \frac{\exp(i\gamma)}{\sqrt{2}} \begin{bmatrix} 1 \\ 1 \end{bmatrix} \quad (88)$$

The result coincides with the conventional Jones vector representation.

These are special cases, but from the above discussions, the validity of eq.(43), the Jones vector representation in terms of the normalized Stokes vector is confirmed.

Next, the method of evaluating polarization properties based on the above general approach will be shown. Here we assume that the measured light is perfectly polarized, and thus use only the normalized Stokes vector. The launched light has states of polarization chosen as linear polarized light whose azimuth angles are 0 deg., 90 deg., and 45 deg., referred as polarized states A, B and C. These are represented as shown in eq.(17). The corresponding output states of polarization are put in the Stokes vector representation shown in eq.(45). Combining the eq.(43) and matrix (22), the following relations are derived according to the Jones calculus.

$$\xi_{out}^A = \begin{bmatrix} u_1 \\ -u_2^* \end{bmatrix} = \frac{\exp(i\gamma_A)}{\sqrt{2(1+S_1^A)}} \begin{bmatrix} 1+S_1^A \\ S_2^A + iS_3^A \end{bmatrix} \quad (89)$$

$$\xi_{out}^B = \begin{bmatrix} u_2 \\ u_1^* \end{bmatrix} = \frac{\exp(i\gamma_B)}{\sqrt{2(1+S_1^B)}} \begin{bmatrix} 1+S_1^B \\ S_2^B + iS_3^B \end{bmatrix} \quad (90)$$

$$\xi_{out}^C = \frac{1}{\sqrt{2}} \begin{bmatrix} u_1 + u_2 \\ u_1^* - u_2^* \end{bmatrix} = \frac{\exp(i\gamma_C)}{\sqrt{2(1+S_1^C)}} \begin{bmatrix} 1+S_1^C \\ S_2^C + iS_3^C \end{bmatrix} \quad (91)$$

In the following discussions, the method of determining the Jones matrix elements is based on the above relationships. Combining eq. (89) and (90), the Jones matrix elements can be rewritten as functions of the Stokes vectors with the absolute phase constant $\gamma$, $$u_1 = \frac{1+s_1^A}{\sqrt{2(1+s_1^A)}} \exp(i\gamma_A) \quad (92)$$

$$u_1^* = \frac{s_2^B + is_2^B}{\sqrt{2(1+s_1^B)}} \exp(i\gamma_B) \quad (93)$$

$$u_2 = \frac{1+s_1^B}{\sqrt{2(1+s_1^B)}} \exp(i\gamma_B) \quad (94)$$

$$u_2^* = \frac{s_2^A + is_3^A}{\sqrt{2(1+s_1^A)}} \exp(i\gamma_A) \quad (95)$$

From eqs. (92) and (94) the absolute value of the Jones matrix elements can be described as $$|u_1| = \sqrt{\frac{1+s_1^A}{2}}, \quad |u_2| = \sqrt{\frac{1+s_1^B}{2}} \quad (96)$$

Then, once the relative phase between the two elements u 1 and u 2 is determined, there is sufficient information to define a Jones matrix which will satisfy the unitarity condition. However, in practice, this unitarity condition is not generally achieved when using the measured values of the Stokes parameters because of the experimental error. Also, the phase of each element of the Jones matrix is required to fully define the optical medium. A method for determining all the information required to define the Jones matrix from the measured Stokes parameters, including the phase factor, will now be presented. The Jones matrix, determined by this method, automatically satisfies the unitarity condition.

In order to determine the phase factor of each element of the Jones matrix, the following relationships between phase factors can be derived from equations (92)–(95)

$$\frac{u_1^*}{|u_1|} = \exp(-i\gamma_A) = \frac{s_2^B + i s_3^B}{\sqrt{(1+s_1^A)(1+s_1^B)}} \exp(i\gamma_B) \qquad (97)$$

$$\frac{u_2^*}{|u_2|} = \exp(-i\gamma_B) = -\frac{s_2^A + i s_3^A}{\sqrt{(1+s_1^A)(1+s_1^B)}} \exp(i\gamma_A) \qquad (98)$$

where $\gamma$, the effective phase parameter is defined as $\gamma = -\gamma_A - \gamma_B$. This effective phase parameter can also be expressed in the following way by taking the arithmetical mean of the above equation $$\exp(i\gamma) = \frac{(s_2^B - s_2^A) + i(s_3^B - s_3^A)}{\sqrt{(1+s_1^A)(1+s_1^B)}} \qquad (100)$$

If there is no experimental error in the measurement of the Stokes parameters, these expressions can be used to determine the effective phase parameter from the experiments. However, as repeatedly mentioned, there will be always unavoidable experimental error which make these expressions mathematically inconsistent. Namely that the absolute magnitude of the right hand side of these equations are not exactly equal to unity when evaluated using experimentally measured Stokes parameters. On the other hand, it is easy to show that the effective phase parameter can be also expressed as follows $$\exp(i\gamma) = \exp[-i(\gamma_A + \gamma_B)] = -\frac{(s_2^B - s_2^A) + i(s_3^B - s_3^A)}{\sqrt{(s_2^B - s_2^A)^2 + (s_3^B - s_3^A)^2}}$$

The right hand side of this equation has the form whose absolute magnitude is explicitly unity. Thus even if measured Stokes parameters are used to evaluate the right hand side of this expression, it is still mathematically consistent in the sense that the absolute magnitude of the right hand side remains unity. Thus this expression can be used to evaluate the effective phase factor using measured Stokes parameters.

Using equation (100), the Jones matrix can now be written in terms of the Stokes parameters as $$U = \begin{bmatrix} u_1 & u_2 \\ -u_2^* & u_1^* \end{bmatrix} \qquad (101)$$

$$= \frac{1}{\sqrt{2}} \begin{bmatrix} \sqrt{1+s_1^A}\exp(i\gamma_A) & \sqrt{1+s_1^B}\exp(-i\gamma_A - i\gamma) \\ -\sqrt{1+s_1^B}\exp(i\gamma_A + i\gamma) & \sqrt{1+s_1^A}\exp(-i\gamma_A) \end{bmatrix}$$

The determinant of the matrix (101) can be calculated as $$\det U = 1 + \tfrac{1}{2}(s_1^A s_1^B) \qquad (102)$$

It is easily shown that the unitarity condition and eq.(96) leads to the condition $s_1^A = -s_1^B$. Therefore the right hand side of the above determinant equation is unity. However, for cases where measurement errors cause violation of the condition $s_1^A = -s_1^B$, the right hand side of eq.(101), can be normalized as follows $$U = \qquad (103)$$

$$\frac{1}{\sqrt{2+s_1^A+s_1^B}} \begin{bmatrix} \sqrt{1+s_1^A}\exp(i\gamma_A) & \sqrt{1+s_1^B}\exp(-\gamma_A - i\gamma) \\ -\sqrt{1+s_1^B}\exp(i\gamma_A + i\gamma) & \sqrt{1+s_1^A}\exp(-i\gamma_A) \end{bmatrix}$$

This expression for the Jones matrix shows that there is still one unknown parameter $\gamma_A$ to be determined. By combining eq.(103) and eq.(91) the following set of equations are obtained $$\sqrt{1+s_1^C}\, y = \frac{1}{\sqrt{2+s_1^A+s_1^B}}\left[\sqrt{1+s_1^A}\, x + \sqrt{1+s_1^B}\,\frac{\exp(-i\gamma)}{x}\right] \qquad (106)$$

$$\frac{s_2^C + i s_3^C}{\sqrt{1+s_1^C}}\, y = \frac{1}{\sqrt{2+s_1^A+s_1^B}}\left[\sqrt{1+s_1^A}\,\frac{1}{x} - \sqrt{1+s_1^B}\exp(-i\gamma)x\right] \qquad (107)$$

where x and y are defined as follows.

$$x = \exp(i\gamma_A)\ \ y = \exp(i\gamma_C)$$

in order to avoid numerical errors, a further renormalization is used to provide for the precise estimation.

By solving these equations (106) and (107), the phase parameters $\gamma_A$ and $\gamma_B$ can be obtained in terms of the Stokes parameters. Notice that three output Jones vectors are needed to uniquely specify the Jones matrix in terms of the Stokes parameters. However experimental errors do not in all cases cause the absolute magnitude of the solutions x and y to not equal unity. In these cases the normalized value of x can be used $$\exp(i\gamma_A) = \frac{x}{|x|} \qquad (108)$$

instead of eq.(103). It is now straightforward to generalize the above discussions for any arbitrary set of three incident states of polarization. For cases where the polarization dependent losses in the medium are negligible and the degree of polarization of light sufficiently large, the above procedures allow for the use of the symmetry conserving construction approach for the Jones matrices.

A numerical simulation will now be given to demonstrate this estimation technique for polarization properties. In this simulation, the transmission medium consists of two polarization maintaining fibres (PMFs) with finite angular misalignment and with polarization mode coupling. The specifications of the two PMFs are as follows: Beat length of both PMFs is 0.03 m at a wavelength 1550 nm. They have the same linear birefringence that is assumed to be independent of the wavelength. To achieve differential group delay (DGD) times for each fibre of 3.00 ps and 2.00 ps respectively, fibre lengths at 17.419 m and 11.613 m are used. The angular misalignment is set at 30 deg.

From the above specifications, the theoretically estimated Jones matrix elements are $$U(\omega_0) = \begin{bmatrix} 0.5546 + 0.7907i & -0.2328 - 0.1142i \\ 0.2328 - 0.1142i & 0.5546 - 0.7907i \end{bmatrix} \quad (109)$$

where $\omega_o$ is the central frequency and corresponds to the wavelength $\lambda_o=1550$ nm. It is assumed that the polarization dependent loss (PDL) is negligible. The output Stokes parameter resulting from three incident states of polarization given by eq.(17) are as follows $$S_A = \begin{bmatrix} 0.865550 \\ 0.077626 \\ -0.494821 \end{bmatrix}, S_B = \begin{bmatrix} -0.865550 \\ -0.077626 \\ 0.494821 \end{bmatrix}, S_C = \begin{bmatrix} -0.438818 \\ -0.358780 \\ -0.823873 \end{bmatrix} \quad (110)$$

Note that in actual experiments, the measured output Stokes parameters would differ from the theoretical values of eq.(110) due to experimental errors. For this numerical simulation, it is assumed that the results include a 10% relative error, and the following values will be used in this example $$S_A = \begin{bmatrix} 0.81 \\ 0.08 \\ -0.50 \end{bmatrix}, S_B = \begin{bmatrix} -0.79 \\ -0.06 \\ 0.46 \end{bmatrix}, S_C = \begin{bmatrix} -0.40 \\ -0.33 \\ -0.77 \end{bmatrix} \quad (111)$$

The degree of polarization (DOP) of these results is calculated from the relationship $$DOP = \sqrt{S_1^2 + S_2^2 + S_3^2} \quad (112)$$

and provides $DOP_A=0.955$, $DOP_B=0.916$ and $DOP_C=0.928$ respectively. These partially polarized states are treated in a similar manner to perfectly polarized states using the following renormalizing procedure $$s = S/DOP \quad (113)$$

The renormalized Stokes vectors obtained using the above calculation are $$s_A = \begin{bmatrix} 0.85 \\ 0.08 \\ -0.52 \end{bmatrix}, s_B = \begin{bmatrix} -0.86 \\ -0.07 \\ 0.50 \end{bmatrix}, s_C = \begin{bmatrix} -0.43 \\ -0.35 \\ -0.83 \end{bmatrix} \quad (114)$$

Applying eq.(100) to these vectors, generates the effective phase factor as $$exp(i\gamma) = -0.1455 + 0.9894i \quad (115)$$

From which the corresponding matrix of the form shown in eq.(101) is $$U = \begin{bmatrix} 0.9642\exp(i\gamma_A) & -(0.0386 + 0.2624i)\exp(-i\gamma_A) \\ (0.0386 + 0.2624i)\exp(i\gamma_A) & 0.9642\exp(-i\gamma_A) \end{bmatrix} \quad (116)$$

then, using eq.(108) $\gamma_A$ is obtained as $$0.7550y = -0.7089\left\{\frac{0.0544 + 0.3702i}{x} + 1.3602x\right\} \quad (117)$$

and $$-(0.4636 + 1.0994i)y = -0.7089\left\{\frac{1.3602}{x} + (0.0544 - 0.3702i)x\right\} \quad (118)$$

The solution of which determines the phase factor where $$x = 0.5845 + 0.8283i \quad (119)$$

$$y = -0.4372 - 0.9014i \quad (120)$$

and the norm of x is $$|x| = 1.0138 \quad (121)$$

and is used to remove the unavoidable numerical errors by normalizing by this quantity to obtain the following results $$\exp(i\gamma_A) = \frac{x}{|x|} = \pm(0.5765 + 0.8171i) \quad (122)$$

and $$U(\omega_0) = \begin{bmatrix} 0.5559 + 0.7878i & -0.2367 - 0.1198i \\ 0.2367 - 0.1198i & 0.5559 - 0.7878i \end{bmatrix} \quad (123)$$

The result is in good agreement with the ideal value shown in eq.(109) wit relative error less than 5%. Alternatively, if the positive value of eq.(122) is used, the result is same, except that an absolute phase difference of $\pi$ is added. This absolute phase difference never influences the polarization characteristics derived from the Jones matrix.

Next, we consider the measurement of polarization mode dispersion for the above system: Two polarization maintaining fibres (PMFs) with fmite angular misalignment are considered. The differential group delay (DGD) time of the principal states of polarization (PSPs), expressed in terms of the elements of the Jones matrix described in eq.(21), are $$\Delta\tau = \frac{1}{\pi}\sqrt{\left|\frac{du_1}{df}\right|^2 + \left|\frac{du_2}{df}\right|^2} \quad (124)$$

where f is the frequency of light. The theory of PSP assumes the unitarity of the Jones matrix for the measured optical transmission medium. In this case, according to the Jones matrix measurement technique shown in the above discussions, Heffners exponential approximation is not necessary. In this two PMF concatenation model, the DGD times of PSPs are calculated as $$\Delta\tau = \sqrt{(\Delta\tau_1 + \Delta\tau_2)^2\cos^2\theta + (\Delta\tau_1 - \Delta\tau_2)^2\sin^2\theta} \quad (125)$$

where $\Delta\tau_1$ and $\Delta\rho_2$ are DGD times of the PSPs for each PMF respectively and $\theta$ is the misalignment angle for concatenation(reference[8]). Thus putting $\theta=30$ deg., DGD time of PSP calculated from eq.(125), is $$\Delta\tau = 4.359 \, ps \quad (126)$$

Next, a numerical simulation of polarization mode dispersion (PMD) measurements will be considered for a situation in which the Stokes parameter is misestimated with the relative error 10%. In eq.(124), the Jones matrix components are differentiated with respect to the frequency of light. In order to estimate these derivatives using the finite differential approximation approach, measurements will be made at two wavelength $\lambda_o=1550.0$ nm and $\lambda_{-1}=1550.2$ nm.

Thus the frequency stepsize is $\Delta f=24.97$ GHz. The output Stokes vectors corresponding to three incident states of polarization eq.(17) should be $$s_{A0} = \begin{bmatrix} 0.8655 \\ 0.0776 \\ -0.4947 \end{bmatrix}, s_{B0} = \begin{bmatrix} -0.8655 \\ -0.0776 \\ 0.4947 \end{bmatrix}, s_{C0} = \begin{bmatrix} -0.4387 \\ -0.3588 \\ -0.8239 \end{bmatrix}, \quad (127)$$

(at $\lambda = \lambda_0$)

and $$s_{A1} = \begin{bmatrix} 0.9678 \\ 0.0186 \\ -0.2512 \end{bmatrix}, s_{B1} = \begin{bmatrix} -0.9678 \\ -0.0186 \\ 0.2512 \end{bmatrix}, s_{C1} = \begin{bmatrix} -0.1241 \\ -0.8325 \\ -0.5399 \end{bmatrix}, \quad (128)$$

(at $\lambda = \lambda_1$)

However, for this simulation, the measured and renormalized Stokes vectors are considered to be $$s_{A0} = \begin{bmatrix} 0.85 \\ 0.08 \\ -0.52 \end{bmatrix}, s_{B0} = \begin{bmatrix} -0.86 \\ -0.07 \\ 0.50 \end{bmatrix}, s_{C0} = \begin{bmatrix} -0.43 \\ -0.35 \\ -0.83 \end{bmatrix}, \quad (129)$$

(at $\lambda = \lambda_0$)

and $$s_{A1} = \begin{bmatrix} 0.97 \\ 0.02 \\ -0.23 \end{bmatrix}, s_{B1} = \begin{bmatrix} -0.97 \\ -0.02 \\ 0.26 \end{bmatrix}, s_{C1} = \begin{bmatrix} -0.12 \\ -0.86 \\ -0.50 \end{bmatrix}, \quad (130)$$

(at $\lambda = \lambda_1$)

Using eqs.(129) and (130), the Jones matrix construction procedure generates the following matrices $$U(\lambda_0) = \begin{bmatrix} 0.5559 + 0.7878i & -0.2367 - 0.1198i \\ 0.2367 - 0.1198i & 0.5559 - 0.7878i \end{bmatrix}, \quad (131)$$

(at $\lambda = \lambda_0$)

and $$U(\lambda_1) = \begin{bmatrix} 0.2656 + 0.9563i & -0.1203 - 0.0231i \\ 0.1203 - 0.0231i & 0.2656 - 0.9563i \end{bmatrix}, \quad (132)$$

(at $\lambda = \lambda_1$)

Then the partial difference approximations provides $$\frac{du_1}{df} = \frac{u_1(\lambda_1) - u_1(\lambda_0)}{\Delta f} = (11.630 - 6.754i) \times 10^{-12} \quad (133)$$

and $$\frac{du_2}{df} = \frac{u_2(\lambda_1) - u_2(\lambda_0)}{\Delta f} = -(4.662 - 3877i) \times 10^{-12} \quad (134)$$

From which the DGD time of PSPs can be estimated as $$\Delta\tau = 4.696 \, ps \quad (135)$$

which is consistent with the result of eq.(126) with a relative error of 10%.

Figure 2:
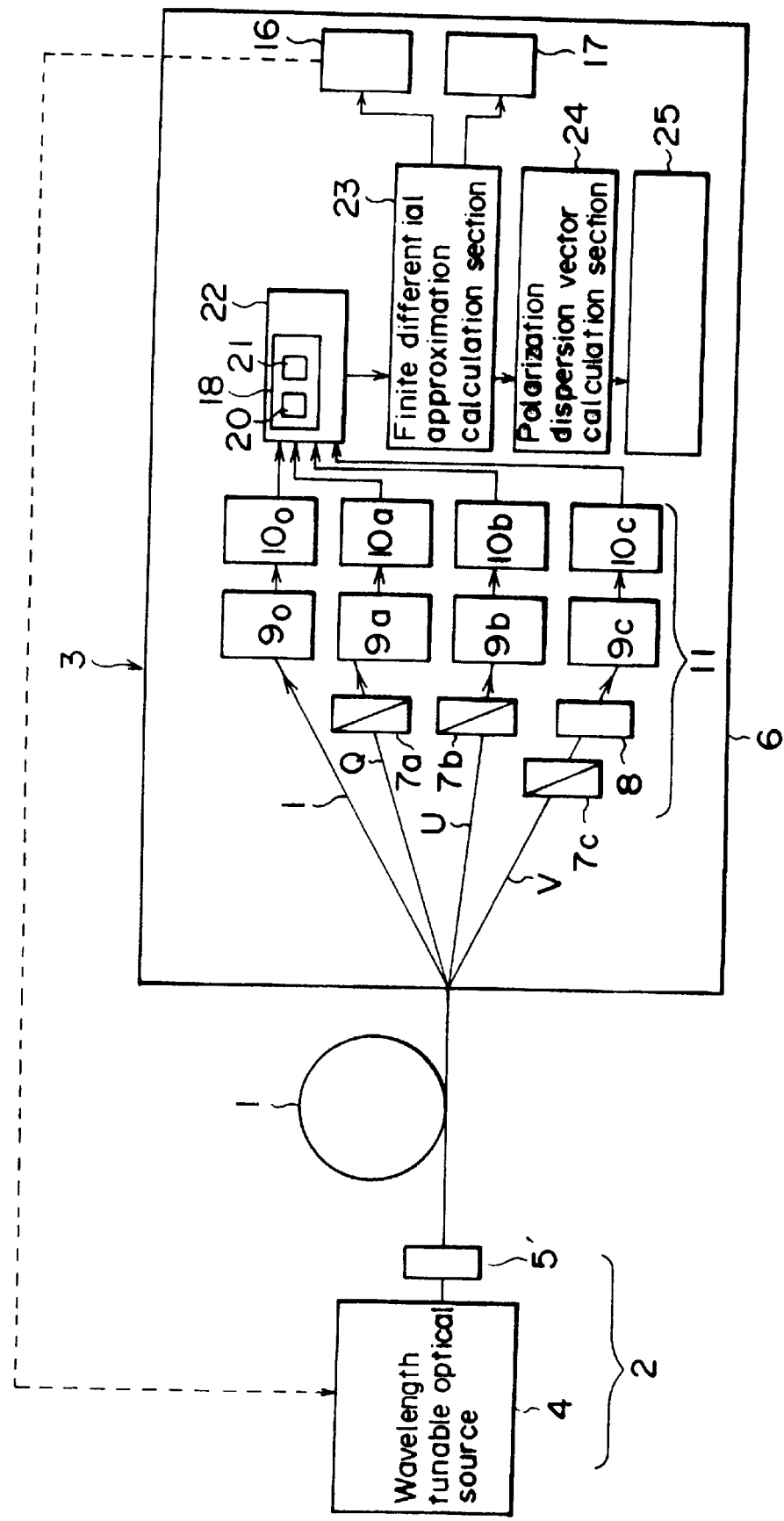
FIG. 2 is a block diagram showing the fundamental parts of an apparatus of an embodiment of the present invention which evaluates polarization dispersion vector and the differential group delay time of the principal states of polarization in polarization mode dispersion analysis.

Next, based on FIG. 2 the fundamental parts of an application of an embodiment of an apparatus to the measurent of DGD time of PSPs of light transmitted through a medium will be described. The polarization measurement apparatus of this embodiment consists of a tunable light source 4, with central wavelength, or angular frequency of ω. Polarization controller 5' where the state of polarization of the light from the tunable source is changed and controlled. The controller 5' must be able to generate at least 3 different states of polarization from any arbitrary input polarization state. The optical light whose state of polarization is controlled by controller 5', is launched into the optical transmission medium 1.

The output-side device 3 consists of the output light measurement means 11 included in the main body 6, the Jones matrix estimation section 22, the finite difference approximation calculation section 23, the polarization dispersion vector calculation section 24, the DGD time of PSP calculation section 25, the measurement accuracy estimation section 17, and the angular frequency control section 16 used to control the tunable light source 4.

The output light measurement means 11, consists of analyzers 7a, 7b, and 7c, a quarter wave plate 8 with no gradient of the azimuth angle, optical intensity detecting section 9$_0$, 9a, 9b, and 9c and corresponding electrical interfaces 10$_0$, 10a, 10b, and 10c. The light transmitted through the optical transmission medium 1, being the object under study, is split into 4 portions designated I, Q, U and V.

Portion I is passed directly to the optical intensity detection section 9$_0$ with its corresponding electrical interface 10$_0$, which measures the overall intensity of the light emerging from the optical transmission medium. The signal representing this intensity is then passed to the Stokes vector normalization section 12, and represents the Stokes vector element I.

Portion Q is passed to analyzer 7a, which is arranged so as to pass light to the optical intensity detection section 9a, with its corresponding electrical interface 10a, the intensity of which represents the difference in intensities between the horizontal and the vertical linearly polarized components of the light emerging from the optical transmission medium. The signal representing this intensity is then passed to the Stokes vector normalization Section 18, and represents the Stokes vector element Q.

Portion U is passed to analyzer 7b, which is arranged so as to pass light to the optical intensity detection section 9b with its corresponding electrical interface 10b, the intensity of which represents the difference in intensities between the linearly polarized components oriented at +45° and −45° of the light emerging from the optical transmission medium. The signal representing this intensity is then passed to the Stokes vector normalization section 18, and represents the Stokes vector element U.

Portion V is passed to a combination of optical elements comprising analyzer 7c and quarter wave plate 8, which are arranged so as to pass light tot eh optical intensity detection section 9c with its corresponding electrical interface 10c, the intensity of which represents the difference in intensities between the right and the left circularly polarized components of the light emerging from the optical transmission medium. The signal representing this intensity is then passed to the Jones matrix calculation section 22, and represents the Stokes vector element V.

The Jones matrix calculation section 22 contains the Stokes vector normalization section 18 which comprises the first normalization section 20 and the second normalization section 21. In the first normalization section 20, the Stokes elements (I, Q, U, V) are normalized in the following manner $$S_1 = Q/I, \, S_2 = U/I, \, S_3 = V/I$$

In the second normalization section the normalized Stokes elements are renormalized as $$s_i = \frac{S_i}{\sqrt{S_1^2 + S_2^2 + S_3^2}}, (i = 1, 2, 3) \tag{136}$$

The Jones matrix calculation section 22 is the section where the Jones matrix, which describes the polarization properties of the optical transmission medium 1, is constructed using the normalized output Stokes vectors. As mentioned, the three different input polarizations A, B, C and their corresponding output states of polarization represented by Stokes vectors, allows for the construction of the unitary matrix from the output Stokes vectors as shown in eq.(13). According to this construction scheme, the matrix at angular frequency $\omega$; $U(\omega)$ and at $\omega+\Delta\omega$; $U(\omega+\Delta\omega)$ are obtained from these measurements, where $\Delta\omega$ is chosen to satisfy the finite differential approximation requirements.

Finite differential approximation calculation section 23 is the section by which the matrices $U(\omega)$ and $U(\omega+\Delta\omega)$ obtained from Jones matrix calculation section 22 are utilized in order to estimate the characteristic hermitian matrix H shown in eq.(57) using finite difference approximation.

The polarization dispersion vector calculation section 24 is the section where the polarization dispersion vector is estimated from the matrix H.

The polarization mode dispersion calculation section 25 is the section by which the DGD time of PSPs, $\Delta\tau$ are estimated from the calculation of the norm of the polarization dispersion vector $\Omega$, obtained from the polarization dispersion vector calculation section 24.

The automatic angular frequency setting section 16 is the section where the absolute value of the ratio of imaginary and real parts of the diagonal term of the matrix H is calculated. The magnitude of this ratio is evaluated to determine whether it is smaller than $\eta$, where $\eta$ must satisfy the condition: $0 \leq \eta \leq 1$. If the ratio is larger than $\eta$, the frequency stepsize $\Delta\omega$ is too large and the estimated $\Delta\tau$ value considered not acceptable. This result is used to control the tunable light source 4 and reduce the frequency step-size $\Delta\omega$ in order to satisfy the condition that the ratio is smaller than $\eta$. Repetition of this feedback procedure leads us to the suitable step size estimation and accurate estimation of the polarization mode dispersion.

The measurement accuracy estimation section 17 is the section where the absolute value of the ratio of the imaginary and real parts of the diagonal terms of the matrix H is calculated in a similar manner to the automatic angular frequency setting section 16. When the magnitude of this ratio is sufficiently smaller than the unity, the polarization mode dispersion measurements can be made with sufficient accuracy.

The embodiment of an apparatus for using the method of obtaining the characteristics of an optical transmission medium to further measuring polarization mode dispersion according to this invention has been constituted as described above, and now an example of the measurement of the polarization mode dispersion for light transmittal through medium 1 by this apparatus will be shown.

Initially, in his embodiment, a test is made of the degree of polarization (DOP) of the light after it has passed through the optical transmission medium under test. If the estimated DOP is sufficiently large, then the PMD (polarization mode dispersion) is measured according to the following manner. In order to evaluate the Jones matrix of the medium, three different incident states of polarization are considered. As described in the preceding discussion, the launched states of polarization are chosen as the linearly polarized light whose azimuth angle are 0 deg., 90 deg., and 45 deg., referred as state of polarization A, B and C. These states of polarization, in the form of Jones vector, are represented as $$\xi_A = \begin{bmatrix} 1 \\ 0 \end{bmatrix}, \xi_B = \begin{bmatrix} 0 \\ 1 \end{bmatrix}, \xi_C = \frac{1}{\sqrt{2}} \begin{bmatrix} 1 \\ 1 \end{bmatrix} \tag{137}$$

The corresponding output states of polarization represented by renormalized Stokes vectors are put as $$s_A = \begin{bmatrix} s_1^A \\ s_2^A \\ s_3^A \end{bmatrix}, s_B = \begin{bmatrix} s_1^B \\ s_2^B \\ s_3^B \end{bmatrix}, s_C = \begin{bmatrix} s_1^C \\ s_2^C \\ s_3^C \end{bmatrix} \tag{138}$$

Combining the eq.(43) and matrix (22), the following relations are derived according to the Jones calculus.

For (A), the 0 deg. linearly polarized state $$\xi_{out}^A = \begin{bmatrix} u_1 \\ -u_2^* \end{bmatrix} = \frac{\exp(i\gamma_A)}{\sqrt{2(1+s_1^A)}} \begin{bmatrix} 1+s_1^A \\ s_2^A + is_3^A \end{bmatrix} \tag{139}$$

For (B), the 90 deg. linearly polarized state $$\xi_{out}^B = \begin{bmatrix} u_2 \\ u_1^* \end{bmatrix} = \frac{\exp(i\gamma_B)}{\sqrt{2(1+s_1^B)}} \begin{bmatrix} 1+s_1^B \\ s_2^B + is_3^B \end{bmatrix} \tag{140}$$

For (C), the 45 deg. linearly polarized state $$\xi_{out}^C = \frac{1}{\sqrt{2}} \begin{bmatrix} u_1 + u_2 \\ u_1^* - u_2^* \end{bmatrix} = \frac{\exp(i\gamma_C)}{\sqrt{2(1+s_1^C)}} \begin{bmatrix} 1+s_1^C \\ s_2^C + is_3^C \end{bmatrix} \tag{141}$$

In the following discussions, the method of determining the Jones matrix elements is based on the above relations.

Combining eq. (139) and (140), the Jones matrix elements can be written as fictions of the Stokes vectors with the absolute phase constant $\gamma$, $$u_1 = \frac{1+s_1^A}{\sqrt{2(1+s_1^A)}} \exp(i\gamma_A) \tag{142a}$$

$$u_1^* = \frac{s_2^B + is_2^B}{\sqrt{2(1+s_1^B)}} \exp(i\gamma_B) \tag{142b}$$

$$u_2 = \frac{1+s_1^B}{\sqrt{2(1+s_1^B)}} \exp(i\gamma_B) \tag{142c}$$

$$u_2^* = \frac{s_2^A + is_3^A}{\sqrt{2(1+s_1^A)}} \exp(i\gamma_A) \tag{142d}$$

From eqs. (142a) and (142c), the absolute value of the Jones matrix elements can be described as $$|u_1| = \sqrt{\frac{1+s_1^A}{2}}, |u_2| = \sqrt{\frac{1+s_1^B}{2}}$$

Then once the relative phase between these two elements $u_1$ and $u_2$ is determined, there is sufficient and complete information from which the Jones matrix which satisfies the unitarity condition can be calculated. However, in practice, the unitarity condition is not satisfied in general if the measured values of the Stokes parameters are used due to experimental error. Furthermore the phase of each element of the Jones matrix is required for the specification of the optical medium to be uniquely specified. A method for the determination of all the required information about Jones matrix, including the phase factor, based on the use of the measured Stokes parameters is now given. The Jones matrix determined by this method automatically satisfies the unitarity condition.

In order to express the phase factor of each element of the Jones matrix, use is made of the following relationship between the phase factors derived by equations (92)–(95)

$$\frac{u_1^*}{|u_1|} = \exp(-i\gamma_A) = \frac{s_2^B + is_3^B}{\sqrt{(1+s_1^A)(1+s_1^B)}} \exp(i\gamma_B) \qquad (143)$$

$$\frac{u_2^*}{|u_2|} = \exp(-i\gamma_B) = -\frac{s_2^A + is_3^A}{\sqrt{(1+s_1^A)(1+s_1^B)}} \exp(i\gamma_A) \qquad (144)$$

where the effective phase parameter $\gamma$ defined as $\gamma = \gamma_A - \gamma_B$ is used. This effective phase parameter can also be expressed in the following way by taking the arithmetical mean of the above equation $$\exp(i\gamma) = \frac{(s_2^B - s_2^A) + i(s_3^B - s_3^A)}{\sqrt{(1+s_1^A)(1+s_1^B)}} \qquad (145)$$

If there is no experimental error in the measurement of the Stokes parameters, any of these expressions can be used to determine the effective phase parameter from the measurements. However, as has been mentioned before, there will be always unavoidable experimental errors which make these expressions mathematically inconsistent. Namely that the absolute magnitude of the right hand side of these equations are not exactly equal to unity when these expressions are developed from experimentally measured Stokes parameters. Alternatively, it is easy to show that the effective phase parameter can be also expressed as $$\exp(i\gamma) = \exp[-i(\gamma_A + \gamma_B)] = -\frac{(s_2^B - s_2^A) + i(s_3^B - s_3^A)}{\sqrt{(s_2^B - s_2^A)^2 + (s_3^B - s_3^A)^2}} \qquad (146)$$

The right hand side of this equation has the form whose absolute magnitude is always unity. Thus even if the measured Stokes parameters are used to evaluate the right band side of this expression, it is still mathematically consistent in the sense that the absolute magnitude of the right hand side remains unity. Thus this expression will be used to evaluate the effective phase factor when using measured Stokes parameters.

Using equation(100), the Jones matrix can be written in terms of the Stokes parameters $$U = \begin{bmatrix} u_1 & u_2 \\ -u_2^* & u_1^* \end{bmatrix}$$

-continued $$= \frac{1}{\sqrt{2}} \begin{bmatrix} \sqrt{1+s_1^A} \exp(i\gamma_A) & \sqrt{1+s_1^B} \exp(-\gamma_A - i\gamma) \\ -\sqrt{1+s_1^B} \exp(i\gamma_A + i\gamma) & \sqrt{1+s_1^A} \exp(-i\gamma_A) \end{bmatrix}$$

and the determinant of this matrix can be calculated as $$\det U = 1 + \frac{1}{2}(s_1^A + s_1^B) \qquad (147)$$

It is easily shown that the unitarity condition and the equations $$|u_1| = \sqrt{\frac{1+s_1^A}{2}}, |u_2| = \sqrt{\frac{1+s_1^B}{2}}$$

lead to the condition $s_1^A = -s_1^B$. Therefore the right hand side of the above deter ant equation(147) is unity. However, measurement errors cause violation of the condition $s_1^A = -s_1^B$, therefore the right hand side of the matrix must be normalized as follows $$U = \frac{1}{\sqrt{2+s_1^A+s_1^B}} \begin{bmatrix} \sqrt{1+s_1^A} \exp(i\gamma_A) & \sqrt{1+s_1^B} \exp(-i\gamma_A - i\gamma) \\ -\sqrt{1+s_1^B} \exp(i\gamma_A + i\gamma) & \sqrt{1+s_1^A} \exp(-i\gamma_A) \end{bmatrix}$$

This expression for the Jones matrix shows that there is one unknown parameter $\gamma_A$ which is discussed below. Combining the above matrix expression with eq.(141) provides the following set of equations $$\sqrt{1+s_1^C} \, y = \frac{1}{\sqrt{2+s_1^A+s_1^B}} \left[ \sqrt{1+s_1^A} \, x + \sqrt{1+s_1^B} \, \frac{\exp(-i\gamma)}{x} \right] \qquad (148a)$$

$$\frac{s_2^C + is_3^C}{\sqrt{1+s_1^C}} \, y = \frac{1}{\sqrt{2+s_1^A+s_1^B}} \left[ \sqrt{1+s_1^A} \, \frac{1}{x} - \sqrt{1+s_1^B} \exp(-i\gamma) x \right] \qquad (148b)$$

where x and y are defined as follows.

$$x = \exp(i\gamma_A), y = \exp(i\gamma_C)$$

in order to avoid numerical error, a further renormalization is required to obtain a precise estimate.

By solving these equations(148a) and (148b), the phase parameter $\gamma_A$ and $\gamma_B$ can be obtained in terms of the Stokes parameters. Notice that three output Jones vector are needed to uniquely specify the Jones matrix in terms of the Stokes parameters. However experimental errors do not in all cases cause the absolute magnitude of the solutions x and y to not equal unity in general. In these cases the normalized value of x $$\exp(i\gamma_A) = \frac{x}{|x|} \qquad (149)$$

can be used in the matrix. For cases where the polarization dependent losses of the medium are negligible and the degree of polarization of light is sufficiently large, the above procedure allows for the construction of the symmetry conserving Jones matrix. It is straightforward to generalize the above discussions for any arbitrary set of three incident SOPs. Thus for cases where the polarization dependent losses of the medium are negligible and the degree of polarization of light is sufficiently large, the above procedure provides for the construction of the symmetry conserving Jones matrix.

Since the Jones matrix obtained in the unitary matrix form is applicable for the study of the principal states of polarization it is, as proposed by Poole and Wagner (reference[6]) and the using of the formula obtained by Aso and Ohshima (reference[7]), widely applicable to the study of optical polarization.

In the case of the PMD measurements, Jones matrix measurements at two angular frequencies $\omega$ and $\omega+\Delta\omega$ are necessary where $\Delta\omega$ is the small frequency interval. Then the corresponding matrix $U(\omega)$ and $U(\omega+\Delta\omega)$ leads to the estimation of the characteristic hermitian matrix H defined as $H=2i\ dU/d\omega\ U^+$ by use of finite difference approximations. The estimation of the characteristic hermitian matrix H then enables the polarization dispersion vector $\Omega$ to be expressed as a function of the hermite matrix. Normalization of this polarization dispersion vector then allows for the differential group delay time of the principal states of polarization to be determined.

Figure 3:
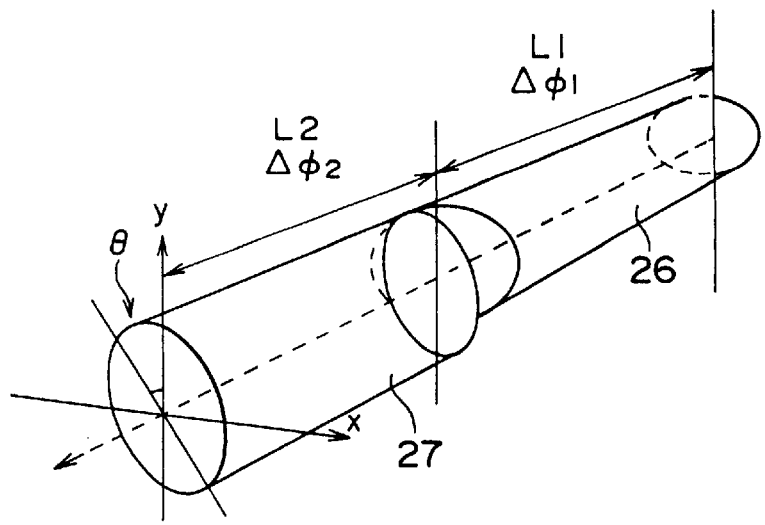
FIG. 3 is a perspective view showing an example of an optical transmission medium for which the polarization mode dispersion is measured in accordance with an application of an embodiment of the present invention.
Figure 4:
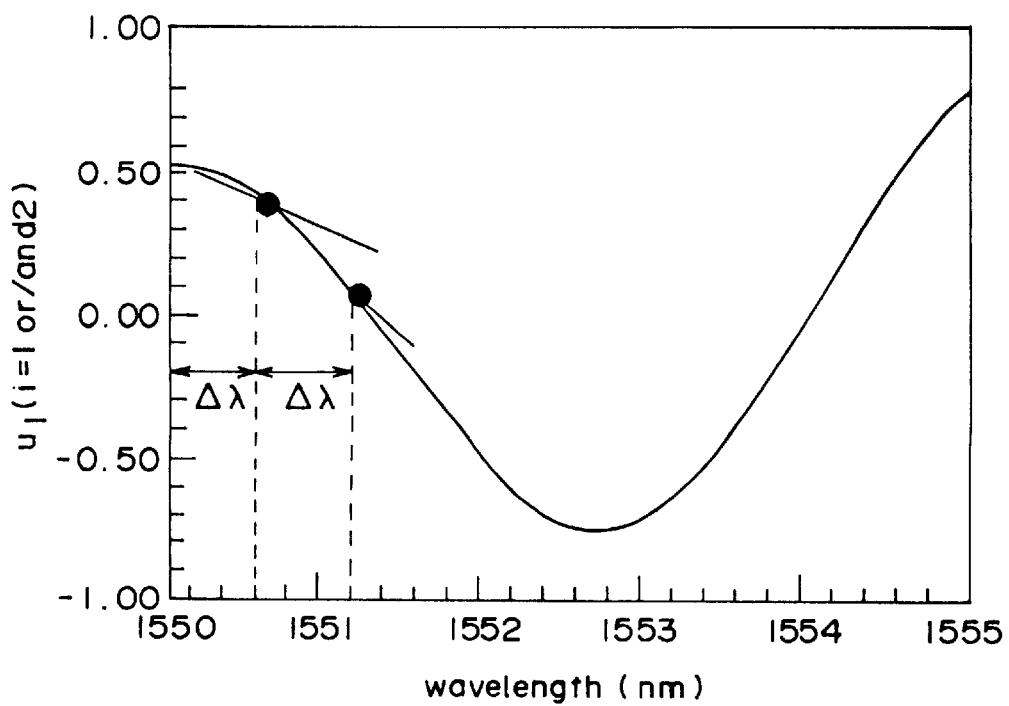
FIG. 4 is an explanatory diagram showing the wavelength dependence of the Jones matrix element ui.
Figure 5:
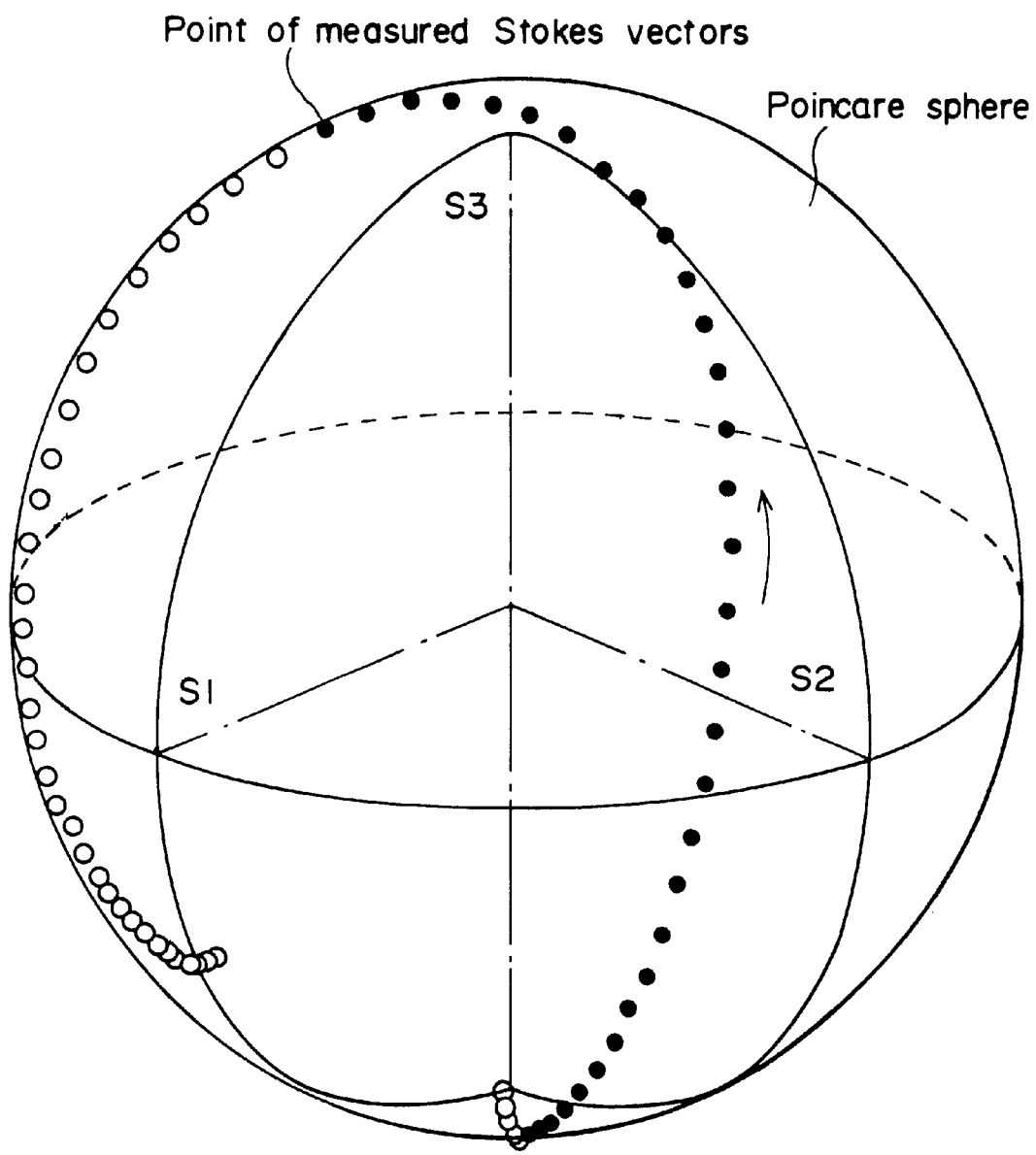
FIG. 5 is an explanatory diagram showing how the trajectory of the Stokes vector, when depicted on a Poincaré sphere, varies with respect to changes in optical wavelength (citation from literature [22])
Figure 6:
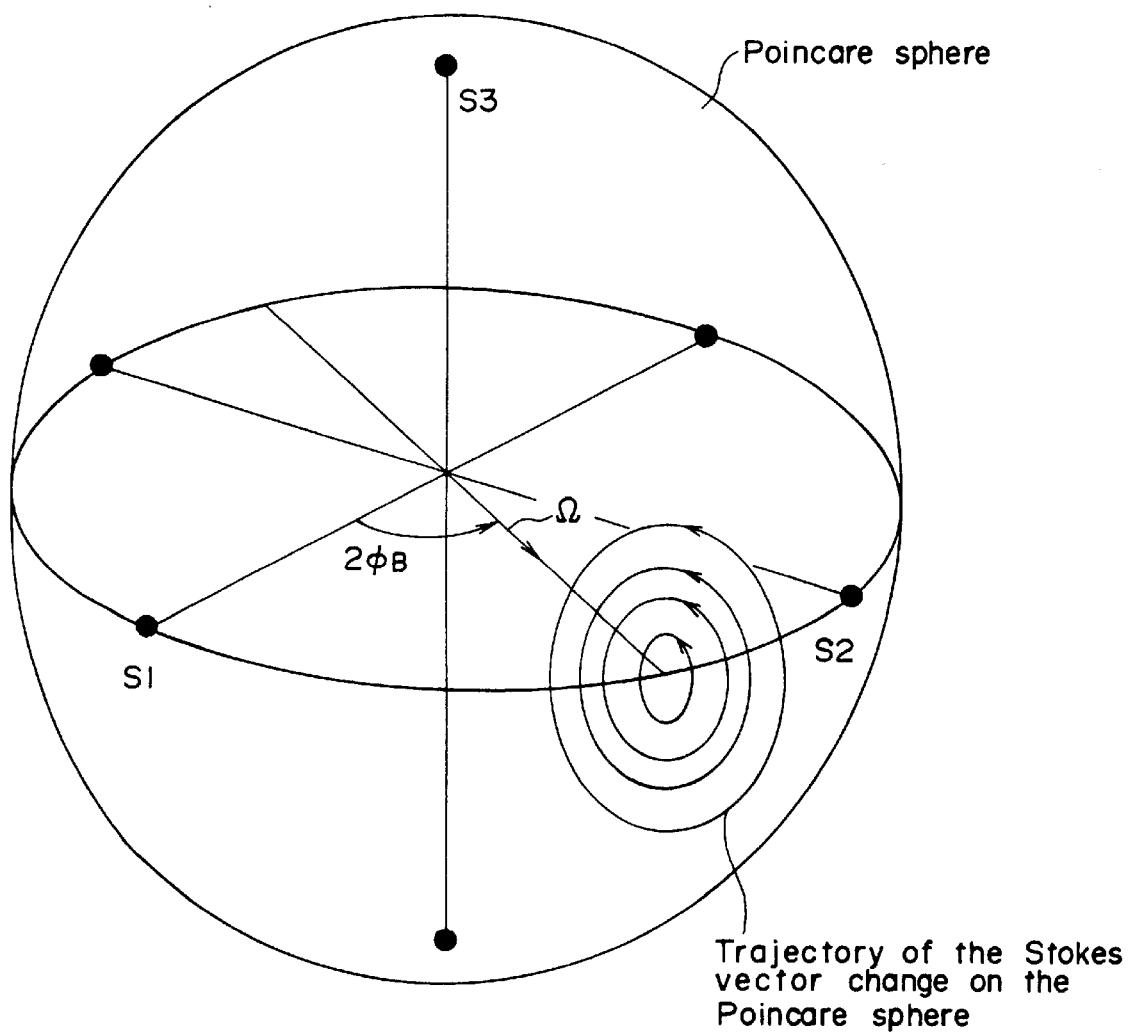
FIG. 6 is an explanatory diagram showing how the trajectory of the Stokes vector, when depicted on Poincaré sphere, varies with respect to changes in optical wavelength (partial recited from literature [16]), for the case where the polarization dispersion vector is independent of frequency, and results in the trajectory following a perfect circle on the sphere (citation from R. Ulrich and A. Simon, "Polarization Optics of Twisted Single-Mode Fibers", Applied Optics, vol. 18, No. 13 (1979) pp. 2241–2251).

Next a numerical example of estimating the differential group delay (DGD) time of principal states of polarization (PSPs) will be presented. This is one of the more important parameters for characterizing the PMD phenomenon. In this example, the transmission medium where polarization mode coupling occurs consists of two polarization maintaining fibres (PMFs) 26 and 27 with finite angular misalignment $\theta$, between their axes as shown in FIG. 3. These fibres have the same linear birefringence which is assumed to be independent of the wavelength and the phase differences of two PMFs are $\Delta\Phi_1$ and $\Delta\Phi_2$ respectively, so that the fibre lengths are chosen as 17.419 m and 11.613 m so that the DGD time of each fibre is 3.00 ps and 2.00 ps respectively. The angular misalignment $\theta$ is set at 30 deg.

Using the valuables $\Delta\Phi_+$ and $\Delta\Phi_-$ where $$\Delta\Phi_+=\Delta\Phi_1+\Delta\Phi_2,\ \Delta\Phi_-=\Delta\Phi_1-\Delta\Phi_2 \quad (150)$$

the elements of the Jones matrix calculated from the Jones analysis are $$u_1=exp(-\Delta\Phi_+)\cos^2\theta+exp(-\Delta\Phi_-)\sin^2\theta \quad (151a)$$

$$u_2=-[exp(-\Delta\Phi_+)+exp(-\Delta\Phi_-)]\sin\theta\cos\theta \quad (151b)$$

Then the characteristic matrix H obtained using eq.(56) has the form shown in eq.(57). The elements of which are described explicitly as $$h_1=\Delta\tau_2\cos 2\theta+\Delta\tau_1(\cos^2 2\theta+\cos\Delta\Phi_2\sin^2 2\theta) \quad (152)$$

$$Re[h_2]=\Delta\tau_2\sin 2\theta+\Delta\tau_1\sin 2\theta\cos 2\theta(1-\cos\Delta\Phi_2\sin^2 2\theta) \quad (153)$$

$$Im[h_2]=-\Delta\tau_1\sin 2\theta\sin\Delta\Phi_2 \quad (154)$$

where $$\Delta\tau_1=\frac{d(\Delta\phi_1)}{d\omega},\ \Delta\tau_2=\frac{d(\Delta\phi_2)}{d\omega} \quad (155)$$

Based on the above results, consider the necessary conditions for first order approximation shown in eq.(74). In practical PMD measurements, the characteristic Hermite matrix H is obtained from the finite differential approximation of the Jones matrix U as:

$$H(\omega)=2i\frac{U(\omega+\Delta\omega)-U(\omega)}{\Delta\omega}U^+(\omega) \quad (156)$$

Using the matrix obtained from (57), where $$\left|\frac{Im[h_1]}{Re[h_1]}\right|\leq\eta \quad (157)$$

is considered the necessary condition. The hermiticity of the matrix H is guaranteed by the existence of the above condition and DGD time of PSPs is estimated according to the eq.(71). In this case, the polarization dispersion vector is obtained explicitly in the form of eq.(70).

In the case of the concatenation of two PMFs (polarization maintaining fibres) as shown in FIG. 3 and described above, the elements of the theoretically obtained Jones matrix are $$u_1(\omega)=0.25[exp(-25.00\times10^{-12}i\omega)+3exp(-12.500\times10^{-12}i\omega)] \quad (158)$$

$$u_2(\omega)=0.433[exp(-25.00\times10^{-12}i\omega)-exp(-12.500\times10^{-12}i\omega)] \quad (159)$$

In practical measurements, the influences of the following errors are unavoidable; (i) an error resulting because the specified incident state of polarization is not exactly realized and (ii) an error caused by the small influences from the negligible but not eliminated polarization dependent losses (PDL). For this example, it is assumed that the total influence of the unavoidable measurement errors is less than 10%. Furthermore, it is assumed that the estimated values of the PDL and the degree of polarization (DOP) for the light after passing through the optical transmission medium, are PDL less than 0.01 dB and DOP greater than 90%. (Light with a DOP value greater than 90% is treated as if it were perfectly polarzed light). Thus the renormalization scheme shown in eq.(136) is applicable. At the wavelength $\lambda=1550$ nm, the Jones matrix of the medium is calculated as $$U(\omega_0)=\begin{bmatrix} 0.5546+0.7907i & -0.2328-0.1142i \\ 0.2328-0.1142i & 0.5546-0.7907i \end{bmatrix} \quad (160)$$

where $\omega_o$ is the central frequency corresponds to the wavelength $\lambda_o=1550$ nm. The output Stokes parameters resulting from three incident states of polarization given by eq.(137) are as follows $$S_A=\begin{bmatrix} 0.865550 \\ 0.077626 \\ -0.494821 \end{bmatrix},\ S_B=\begin{bmatrix} -0.865550 \\ -0.077626 \\ 0.494821 \end{bmatrix},\ S_C=\begin{bmatrix} -0.438818 \\ -0.358780 \\ -0.823873 \end{bmatrix} \quad (161)$$

In the actual experiments the measured output Stokes parameters are different from the theoretical value in eq. (110) due to experimental errors. The Stokes vectors after renormalization and including the assumed 10% relative error are $$s_A=\begin{bmatrix} 0.85 \\ 0.08 \\ -0.52 \end{bmatrix},\ s_B=\begin{bmatrix} -0.86 \\ -0.07 \\ 0.50 \end{bmatrix},\ s_C=\begin{bmatrix} -0.43 \\ -0.35 \\ -0.83 \end{bmatrix} \quad (162)$$

Using these vectors with eq.(78) and eq.(46) provides the effective phase factor as $$exp(i\gamma)=-0.1455+0.9894i \quad (163)$$

Using the eq.(163), the corresponding matrix as given by eq.(101) is $$U = \begin{bmatrix} 0.9642\exp(i\gamma_A) & -(0.0386+0.2624i)\exp(-i\gamma_A) \\ (0.0386+0.2624i)\exp(i\gamma_A) & 0.9642\exp(-i\gamma_A) \end{bmatrix} \quad (164)$$

and the equation for obtaining the γA, is obtained from eq.(108) is $$0.7550y = -0.7089\left\{\frac{0.0544+0.3702i}{x} + 1.3602x\right\} \quad (165)$$

and $$-(0.4636+1.0994i)y = -0.7089\left\{\frac{1.3602}{x} + (0.0544-0.3702i)x\right\} \quad (166)$$

Solution of these equations determines tie phase factor where $$x = 0.5845 + 0.8283i \quad (167)$$

$$y = -0.4372 - 0.9014i \quad (168)$$

and the numerical unavoidable error, the norm of x is $$|x| = 1.0138 \quad (169)$$

uing this quantity to normalize by, provides the following results $$\exp(i\gamma_A) = \frac{x}{|x|} = \pm(0.5765 + 0.8171i) \quad (170)$$

and $$U(\omega_0) = \begin{bmatrix} 0.5559+0.7878i & -0.2367-0.1198i \\ 0.2367-0.1198i & 0.5559-0.7878i \end{bmatrix} \quad (171)$$

This result is in good agreement with the ideal value shown in eq.(160) and has a relative error smaller than 5%. Alternatively, if the positive value of eq.(170) is used, the result is same except that an absolute phase difference of 7 is added. This absolute phase difference never influences the polarization characteristics derived from the Jones matrix.

Similarly, consider the calculation of the Jones matrix using measurements taken at a wavelength of λ1552 nn, were a Δλ=2.0 nm. For this case, the output normalized Stokes vectors for the three states of polarized light after passing through the medium are theoretically calculated as $$S_A = \begin{bmatrix} -0.3624 \\ 0.7866 \\ 0.4999 \end{bmatrix}, S_B = \begin{bmatrix} 0.3624 \\ -0.7866 \\ -0.4999 \end{bmatrix}, S_C = \begin{bmatrix} 0.9289 \\ 0.2611 \\ 0.2625 \end{bmatrix} \quad (172)$$

when a relative error of 10% is included to simulate actual experimental measurements, and the normalized vectors renormalized, this provides $$s_A = \begin{bmatrix} -0.36 \\ 0.80 \\ 0.48 \end{bmatrix}, s_B = \begin{bmatrix} 0.35 \\ -0.79 \\ -0.51 \end{bmatrix}, s_C = \begin{bmatrix} 0.93 \\ 0.26 \\ 0.27 \end{bmatrix} \quad (173)$$

Using the procedure for Jones matrix determination described above, the estimated matrix is $$U(\omega_0 + \Delta\omega) = \begin{bmatrix} -0.1307-0.5518i & -0.2625-0.7807i \\ 0.2625-0.7807i & -0.1307+0.5518i \end{bmatrix} \quad (174)$$

where $\Delta\omega = -1.5671012$ rad./sec. corresponding to $\Delta\lambda = 2.0$ nm.

The derivative of U, with respect to the angular frequency, is calculated by finite difference approximation as $$\frac{dU}{d\omega} = \frac{U(\omega_0+\Delta\omega) - U(\omega_0)}{\Delta\omega} = $$
$$10^{-12} \times \begin{bmatrix} -0.2713-0.1506i & 0.3185+0.5746i \\ -0.3185+0.5746i & -0.2713+0.1506i \end{bmatrix} \quad (175)$$

The characteristic hermitian matrix obtained as $$H(\omega_0) = 2i\frac{dU}{d\omega}U^+ = 2i\frac{U(\omega_0+\Delta\omega)-U(\omega_0)}{\Delta\omega}U^+(\omega_0) \quad (176)$$
$$= 10^{-12} \times \begin{bmatrix} 0.0644+0.8273i & 1.0044+0.6436i \\ 1.0044-0.6436i & -0.0644+0.8273i \end{bmatrix}$$

from is, the matrix elements are $$h_1(\omega_0) = (0.0644+0.8273i) \times 10^{-12} \quad (177)$$

$$h_2(\omega_0) = (1.044+0.6436i) \times 10^{-12} \quad (178)$$

Theoretically, $h_1$ must be a real number, therefor $h_1 = 0.0644\ 10^{-12}$ is used. Thus the estimated polarization vector is $$\Omega = \begin{bmatrix} 3.9949 \\ 1.9190 \\ -1.2793 \end{bmatrix} \times 10^{-12} \quad (179)$$

From this the estimated DGD time of PSPs is $\Delta\tau = 1.195$ ps, which does not agree with the theoretical value $\Delta\tau = 4.359$ ps. To understand this error consider eq.(177). The ratio defined by eq.(74) of $|\text{Im}[h_1]/\text{Re}[h_1]| = 12.844$ which is significantly larger than 1.000, therefore the $\Delta\omega$ of the above estimation was too large, and precludes the use of the first order approximation approach.

Now, consider the determination of the Jones matrix using measurements made at a wavelength $\lambda = 1550.2$ nm, where a $\Delta\lambda = 0.2$ am is considered. In this case, the output normalized Stokes vectors for the three states of polarized light alter passing through the medium are theoretically calculated as $$S_A = \begin{bmatrix} 0.9678 \\ 0.0186 \\ -0.2512 \end{bmatrix}, S_B = \begin{bmatrix} -0.9678 \\ -0.0186 \\ 0.2512 \end{bmatrix}, S_C = \begin{bmatrix} -0.1241 \\ -0.8325 \\ -0.5399 \end{bmatrix} \quad (180)$$

when a relative error of 10% is included to simulate actual experimental errors, and the normalized vectors renormalized, this provides $$s_A = \begin{bmatrix} 0.97 \\ 0.02 \\ -0.23 \end{bmatrix}, s_B = \begin{bmatrix} -0.97 \\ -0.02 \\ 0.26 \end{bmatrix}, s_C = \begin{bmatrix} -0.12 \\ -0.86 \\ -0.50 \end{bmatrix} \quad (181)$$

Using the procedure for the Jones matrix determination described above, the estimated matrix is $$U(\omega_0 + \Delta\omega) = \begin{bmatrix} -0.2656 - 0.9563i & 0.1203 + 0.0231i \\ -0.1203 + 0.0231i & -0.2656 + 0.9563i \end{bmatrix} \quad (182)$$

Using these results, together with those of eq.(171), to obtain the derivative of U by finite difference approximation, leads to an estimated $h_1 = (3.9949 + 0.86399i)10^{-12}$ and $h2 = (1.9190 + 1.2793i)_{10}^{-2}$. Using a value of $\eta = 0.25$ in eq.(74), the ratio of $|\text{Im}[h_1]/\text{Re}[h_1]| = 0.2163 < 0.25$. Therefore the $\Delta\omega$ used in the above estimation satisfies the requirements for using the first order approximation approach.

The estimated polarization dispersion vector then is $$\Omega = \begin{bmatrix} 3.9949 \\ 1.9190 \\ -1.2793 \end{bmatrix} \times 10^{-12} \quad (183)$$

and the calculated DGD time of PSPs is $\Delta\tau = 4.613$ ps. This result agrees well with the theoretical value $\Delta\tau = 4.359$ ps, with an error less than 5%.

The present invention is not only limited to the aforementioned embodiments but is also applicable to other various embodiments. For example, in the method of evaluating the polarization characteristics, the evaluation of the Jones vector of the output light is described together with the method for evaluating the Jones matrix which represents the the polarization characteristics of an optical transmission medium, such as a single mode optical fibres. However, the methods and apparatus of the present invention are equally appreciable for evaluating the state of polarization of light and polarization characteristics of any medium used in the industrial field where measurements of the state of polarization of light and polarization characteristics of the optical transmission medium are required.

[1] H. Takenaka, "Applications of Functional Theory to Polarization Optics", Nouv. Rev. Optique, vol. 4, No. 1 (1972) pp. 196–201.
[2] C. De Angelis, A. Galtarossa, G. Gianello, F. Matera and M. Schiano, "Time Evolution of Polarization Mode Dipersion in Long Terrestrial Links", Journal of Lightwave Technology, vol. 10, No. 5 (1992) pp. 552–555.
[3] R. C. Jones, "A New Calculus for the Treatment of Optical Systems: VI Experimental Determination of the Matrix", Journal of the Optical Society of America, vol. 37, No. 2 (1947) pp. 110–112.
[4] B. L. Heffner, "Automated Measurement of Polarization Mode Dispersion Using Jones Matrix Eigenanalysis", Photonics Technology Letters, vol. 4, No. 9 (1992) pp. 1066–1069.
[5] B. L. Heffner, "Apparatus and Method for Measuring Polarization", Japan laid Open Publication No. HE14-218735 (1992)
[6] C. D. Poole and R. E. Wagner, "Phenomenological Approach to Polarization Dispersion in Long Single-Mode Fibres", Electronics Letters, vol. 22, No. 19 (1986) pp. 1029–1031.
[7] O. Aso and I. Ohshima, "A Study on The Mode Coupling Effect in Polarization Mode Dispersion Measurements", Meeting Technical Group of Optical Communication Systems IEICE Japan, OCS 94-75 (1994) pp. 87–92 (in Japanese).
[8] O. Aso and H. Nakamura, "Principal States of Polarization: Time Domain Measurements with Coherent Optical Pulse", Electronics Letters, vol. 32, No. 6 (1996) pp. 578–579.
[9] C. R. Menyuk and P. K. A. Wai, "Polarization Evolution and Dispersion with Spatially Varying Birefringence", Journal of the Optical Society of America B, vol. 11, No. 7 (1994) pp. 1283–1292.
[10] O. Aso, I. Ohshima and H. Ogoshi, "A Study on the First Order Effect of the Phenomenological PMD Model in Long DSF", Technical Digest, Fifth Optoelectronics Conference (1994) 14E-2 pp, 238–239.
[11] O. Aso, I. Ohshima and H. Ogoshi, "Study on A Conservation QuantiTY in PMD Measurements", Technical Digest, Symposium on Optical Fiber Measurements (1994) pp, 159–162.
[12] B. M. Nyman and G. Wolter, "High-Resolution Measurement of Polarization Dependent Loss", Photonics Technology Letters, vol. 5, No. 7 (1993) pp. 817–818
[13] N. Mekata, A. Al-Hamadan, T. Murakami and M. Miyoshi, "New Direct Measurement technique of Polarization Dependent Loss with High-Resolution Repeatability", Technical Digest, Symposium on Optical Fiber Measurements (1994) pp, 189–192.
[14] R. Ulrich and A. Simon, "Polarization Optics of Twisted Single-Mode Fibers", Applied Optics, vol. 18, No. 13 (1979) pp. 2241–2251.
[15] S. C. Rashleigh, "Origins and Control of Polarization Effects in Single-Mode Fibers", Journal of Lightwave technology, vol. LT-1, No. 2 (1983) pp. 312–331.
[16] R. M. A. AZZAM and N. M. Bashara, Ellipsometry and Polarized Light, North-Holland Science, B.V., Nether Land (1977)
[17] N. Uesugi, S. Ohashi, Opto-Electronic Measuring Instruments Guide, ed. T. Tayuki and T. Honda (1994).(in Japanese)
[18] D. S. Kliger, J. W. Lewis and C. E. Randall, Polarization Light in Optics and Spectroscopy, Academic Press, (1990)
E. Collet, Polarized Light - Fundamentals and Applications, Marcel Dekker Inc., N.Y., (1993)
[19] H. Georgi, Lie Algebras in Particle Physics, From Isospin to Unified Theories, Benjamin/Cummings Co., Inc., (1982).
C. W. Misner, K. S. Thorne and J. A. Wheeler, Gravitation, Freeman, San Francisco
[20] W. T. Payne, "Elementary Spinor Theory", American Journal of Physics, vol. 20, No. 5 (1952) pp. 253–262.
S. R. Cloude, "Group Theory and Polarization Algebra", OPTIK, vol. 75, No. 1 (1986) pp. 26–36.
[21] A. Yariv and P. Yeh, Optical Waves in Crystals, Wiley, N.Y. (1983)
[22] C. D. Poole, N. S. Bergano, R. E. Wagner and H. J. Schulte, "Polarization Dispersion and Principal States in a 147 km Undersea Lightwave Cable", Journal of Lightwave Technology, vol. 6, No. 7 (1988) pp. 1185–1190.
[23] J. J. Refi, T. E. Darcie, A. F. Judy and C. D. Poole, "Polarization Dispersion and Its Effect on Optical Transmission", 1993 NCTA Technical Papers (1993) pp. 116–121.
[24] N. Gisin, "Polarization Mode Dispersion: Definitions, Measurements and Statistics", Technical Digest-Symposium on Optical Fiber Measurements (1994) pp. 149–154.
[25] N. Gisin and J. P. Pellaux, "Polarization Mode Dispersion: Time versus Frequency Domains", Optics Communications, vol. 89, No. 2,3,4 (1992) pp. 316–323.
[26] W. Eickhoff, Y. Yena and R. Ulrich, "Wavelength dependence of Birefringence in Single-Mode Fibers", Applied Optics, vol. 20, No. 19 (1981) pp. 3428–3435.
[27] R. Ulrich, "Representation of the Codirectional Coupled Waves", Optics Letters, vol. 1, No. 3 (1977) pp. 109–111.
[28] A. Simon and R. Ulrich, "Evolution of Polarization along a Single-Mode Fiber", Applied Physics Letters, vol. 31, No. 8 (1977) pp. 517–520.
[29] G. J. Foschini and C. D. Poole, "Statistical Theory of Polarization Dispersion in Single-Mode Fibers", Journal of Lightwave Technology, vol. 9, No. 11 (1991) pp. 1439–1456.
[30] Hewlett Packard Company, HP8509A/B Lightwave Polarization Analyzer User's Reference Guide, (1992) chap. 2, p. 15, unpublished.
[31] Y. Namihira and H. Wakabayashi, "Fiber Length Dependence of Polarization Mode Dispersion in Long-Length Optical Fibers and Installed Optical Submarine Cables", Journal of Optical Communications, vol. 12, No. 1 (1991) pp. 2–9.
[32] C. Kittel, Introduction to Solid State Physics, 6th edition, John Wiley and Sons (1986) chap. 16
[33] M. Born and E. Wolf, Principles of Optics, 6th edition, Pergamon (1980)
[34] C. D. Poole and C. R. Giles, "Polarization Dependent Pulse Compression and Broadening due to Polarization Dispersion in Dispersion-Shifted Fiber", Optics Letters, vol. 13, No. 2 (1988) pp. 155–157.

What is claimed is:

1. A method to obtain polarization characteristics of an optical transmission medium comprising the steps of launching light of a known state of polarization into the optical transmission medium;

measuring the state of polarization of the light emerging from the optical transmission medium in terms of intensity measurements corresponding to elements of a Stokes vector;

describing the launched light as a Jones vector;

forming a Stokes vector representing the emerging light and normalizing this vector;

transposing the normalized Stokes vector into a normalized Jones vector which describes the emerging light;

repeating the above steps at least two times, and for each using a different polarization for the launched light;

using the Jones vectors, which describe the plural launched input and emerging states of polarization, constructing a Jones matrix $U(\omega)$ which represents the polarization characteristics of the optical transmission medium in a unitary matrix form; and, evaluating the polarization characteristics of the medium in the form of the Jones matrix.

2. The method as defined in claim 1, wherein the method of forming the Jones vectors from the measured Stokes vectors of the form $$S = \begin{bmatrix} I \\ Q \\ U \\ V \end{bmatrix}$$

comprises the normalization of the elements to form the normalized Stokes vectors of the form $$S = \begin{bmatrix} S_1 \\ S_2 \\ S_3 \end{bmatrix}$$

where $S_1 = Q/I$ $S_2 = U/I$ $S_3 = V/I$ which for perfectly polarized light satisfy the condition $S_1^2 + S_2^2 + S_3^2 = 1$ and where the normalized Jones vector is calculated in terms of elements of the normalized Stokes vector as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}, S_1 \neq -1 \text{ and },$$

$$\xi = \begin{bmatrix} \xi_1 \\ \xi_2 \end{bmatrix} = \begin{bmatrix} 0 \\ 1 \end{bmatrix}, S_1 = -1$$

and wherein the former equation reduces the limits of the latter equation under the conditions of a singular state polarization, thus $$\xi = \lim_{S_1 \to -1} = \frac{\exp(i\gamma)}{\sqrt{2(1+S_1)}} \begin{bmatrix} 1+S_1 \\ S_2 + iS_3 \end{bmatrix}, = \exp(i\gamma) \begin{bmatrix} 1 \\ 0 \end{bmatrix}$$

and the normalized Jones vector represented in terms of the normalized Stokes elements is $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}.$$

3. The method as detailed in claim 2, wherein in addition to normalizing the Stokes vector, the normalized Stokes vectors $$S = \begin{bmatrix} S_1 \\ S_2 \\ S_3 \end{bmatrix}$$

are normalized to form $$s = \begin{bmatrix} s_1 \\ s_2 \\ s_3 \end{bmatrix}$$

where $$s_i \equiv \frac{S_i}{\sqrt{S_1^2 + S_2^2 + S_3^2}}, (i = 1, 2, 3)$$

a the normalized Jones vectors formed as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}$$

using the normalized Stokes elements $s_i$ (i=1,2,3).

4. The method as described in claim 1 wherein the intensity measurements corresponding to the elements of the Stokes vector are obtained by separating the emerging light into four portions and directing each to a separate intensity measurement system configured such that each measures a separate Stokes element, and from which the Stokes vectors are constructed.

5. The method of obtaining polarization characteristics of an optical transmission medium as described in claim 3 wherein the normalized Jones vectors $\xi$ are obtained by performing the limiting operation of letting the normalized Stokes vector elements $S_1$ tend towards $-1$, and then using the resultant normalized Stokes vector elements to calculate the normalized Jones vectors as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}$$

$$\xi = \begin{bmatrix} \xi \\ \xi_2 \end{bmatrix} = 0, 1 S_1 = -1$$

6. The method of obtaining polarization characteristics of an optical transmission medium as described in claim 3 wherein normalized Jones vectors $\xi$ are obtained by performing the limiting operation of letting the renormalized Stokes elements tend towards $-1$, and then using the resultant renormalized Stokes vector elements to calculate the normalized Jones vectors as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}.$$

7. A method to obtain polarization characteristics of an optical transmission medium comprising the steps of:

sequentially launching plural different states of polarized light into the optical transmission medium;

measuring intensities of light emerging from the optical transmission medium through combinations of optical elements to obtain Stokes parameters from which Stokes vectors describing the emerging light corresponding to each of the plural sequentially launched states of polarization are obtained; wherein light, which is sequentially constrained to three different states of polarization, A, B, and C, is launched into an optical transmission medium, and where the light constrained to each of the three states of polarization A, B, and C may be described by normalized Jones vectors as $$\xi_A = \begin{bmatrix} \xi_A^1 \\ \xi_A^2 \end{bmatrix}, \xi_B = \begin{bmatrix} \xi_B^1 \\ \xi_B^2 \end{bmatrix}, \xi_C = \begin{bmatrix} \xi_C^1 \\ \xi_C^2 \end{bmatrix}.$$

and where light emerging from the optical transmission medium, corresponding to each input state of polarization, is measured in the form of Stokes elements, from which normalized Stokes vectors $$S_A = \begin{bmatrix} s_1^A \\ s_2^A \\ s_3^A \end{bmatrix}, S_B = \begin{bmatrix} s_1^B \\ s_2^B \\ s_3^B \end{bmatrix}, S_C = \begin{bmatrix} s_1^C \\ s_2^C \\ s_3^C \end{bmatrix}$$

are calculated, which when renormalized provide relationships between the renormalized Stokes vector elements and the normalized Jones vector elements of $$\frac{1+s_1^A}{\sqrt{2(1+s_1^A)}} \exp(i\gamma_A) = u_1 \xi_1^A + u_2 \xi_2^A,$$

$$\frac{1+s_1^B}{\sqrt{2(1+s_1^B)}} \exp(i\gamma_B) = u_1 \xi_1^B + u_2 \xi_2^B,$$

$$\frac{s_2^A + i s_3^A}{\sqrt{2(1+s_1^A)}} \exp(i\gamma_A) = u_1^* \xi_2^A - u_2^* \xi_1^A,$$

and $$\frac{s_2^B + i s_3^B}{\sqrt{2(1+s_1^B)}} \exp(i\gamma_B) = u_1^* \xi_2^B - u_2^* \xi_1^B.$$

which when the implicit constraints of $$|u_1|^2 + |u_2|^2 = 1$$
$$|\xi_1^A|^2 + |\xi_2^A|^2 = 1$$
$$|\xi_1^B|^2 + |\xi_2^B|^2 = 1$$

are applied, and utilizing the variable $\gamma$, where $$\gamma \equiv -\gamma A - \gamma B$$

provides for the matrix U to be formed in terms of the undetermined variable $\gamma A$ as $$U = \begin{bmatrix} u_1 & u_2 \\ -u_2^* & u_1^* \end{bmatrix} = \frac{1}{\sqrt{|m_1|^2 + |m_2|^2}} \begin{bmatrix} m_1(\gamma_A) & m_2(\gamma_A) \\ -m_2^*(\gamma_A) & m_1^*(\gamma_A) \end{bmatrix}$$

and where $\gamma_A$ is determined by utilizing the renormalized Stokes vector Sc elements to generate $$\frac{\exp(i\gamma_C)}{\sqrt{2(1+s_1^C)}} \begin{bmatrix} 1+s_1^C \\ s_2^C + i s_3^C \end{bmatrix} = \frac{1}{\sqrt{2(|m_1|^2 + |m_2|^2)}} \begin{bmatrix} m_1 + m_2 \\ m_1^* - m_2^* \end{bmatrix}$$

with which the parameters $\gamma_A$ and $\gamma_C$ are uniquely determined, and all the matrix elements determined, such that they satisfy the unitary condition for the matrix.

8. A method to obtain polarization characteristics of an optical transmission medium as defined in claim 1, further comprising the steps of determining the polarization mode dispersion (PMD) of that medium comprising the additional steps of:

performing another measurement of the Jones matrix which is the polarization characteristics of the medium using light at a frequency $\Delta\omega$ removed from the frequency of the light used to obtain the first matrix $U(\omega)$, thus obtaining $U(\omega+\Delta\omega)$;

estimating the characteristic hermitian matrix H from $U(\omega)$ and $U(\omega+\Delta\omega)$ by using finite difference approximation, where $$H(\omega) \equiv 2i \frac{dU}{d\omega} U^+$$

calculating the polarization dispersion vector $\Omega$, from the hermite matrix H;

evaluating the polarization mode dispersion in terms of differential group delay times of principal states of polarization which are calculated from the norm of the polarization dispersion vector $\Omega$.

9. The method as described in claim 8, wherein an estimate of measurement accuracy of the differential group delay times of the principal states of polarization is also obtained by determining the amount of depolarization that occurs within the optical transmission medium from separate measurements of the degree of polarization of the launched and emerging light, and from the magnitude of the ratio of the imaginary and real parts of the diagonal elements within the hermitian matrix.

10. The method as set out in claim 8, wherein a magnitude of the difference in frequencies $\Delta\omega$ of the light from which the Jones matrices $U(\omega)$ and $U(\omega+\Delta\omega)$ are constructed, is controlled such that a ratio $\eta$ lies in the region $0 \leq |\eta| \leq 1$, where $\eta$ is the ratio between the imaginary and real parts of the diagonal elements of the hermitian matrix H which is obtained by finite difference approximation from the two Jones matrices $U(\omega)$ and $U(\omega+\Delta\omega)$.

11. An apparatus for obtaining the polarization characteristics of an optical transmission medium comprising:

means for forming plural known polarized states of light, and separately launching these into an optical transmission medium;

means for measuring intensity of the light emerging from the optical transmission medium in terms of Stokes elements, and for forming Stokes vectors and for repeating these measurements for each of the plural polarized states of light launched into the optical transmission medium;

means for computing plural normalized Stokes vectors from the plural Stokes vectors comprising the measured intensities;

means for computing the normalized Jones vectors, describing the launched light;

means for computing a Jones matrix of the optical transmission medium, which represents the polarization characteristics of the optical transmission medium in the form of a unimodular unitary matrix, from the normalized Jones vectors, and with the elements of the Jones matrix evaluated such that geommetrical symmetry of the matrix is achieved.

12. The apparatus as detailed in claim 11, wherein the Stokes vector $$S = \begin{bmatrix} I \\ Q \\ U \\ V \end{bmatrix}$$

obtained by measuring intensities of the emerging light is normalized in a means for computing the normalized Stokes vectors to form the normalized Stokes vectors of the form $$S = \begin{bmatrix} S_1 \\ S_2 \\ S_3 \end{bmatrix}$$

where $S_1 = Q/I$ $S_2 = U/I$ $S_3 = V/I$ and where these elements satisfy the condition $S_1^2 + S_2^2 + S_3^2 = 1$ under conditions of perfect polarization from which the normalized Jones vector is calculated as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix}, S_1 \neq -1 \text{ and,}$$

$$\xi = \begin{bmatrix} \xi_1 \\ \xi_2 \end{bmatrix} = \begin{bmatrix} 0 \\ 1 \end{bmatrix}, S_1 = -1.$$

13. The apparatus as detailed in claim 12 wherein the Stokes vector normalization means further renormalizes the normalized Stokes vector $$S = \begin{bmatrix} S_1 \\ S_2 \\ S_3 \end{bmatrix}$$

to form the renormalized Stokes vector $$s = \begin{bmatrix} s_1 \\ s_2 \\ s_3 \end{bmatrix}$$

where $$s_i \equiv \frac{S_i}{\sqrt{S_1^2 + S_2^2 + S_3^2}}, (i = 1, 2, 3).$$

and wherein the Jones matrix is computed from the plural renormalized Stokes vectors from which the Jones vector is computed as $$\xi = \begin{bmatrix} \xi_1 \\ \xi_2 \end{bmatrix} = \frac{\exp(i\gamma)}{\sqrt{2(1+S_1)}} \begin{bmatrix} 1+S_1 \\ S_2 + iS_3 \end{bmatrix} \quad s_1 \neq -1$$

and, $$\xi = \begin{bmatrix} \xi \\ \xi_2 \end{bmatrix} = 0, 1 \quad s_2 = -1.$$

14. An apparatus for obtaining the polarization characteristics of an optical transmission medium and using these to determine the polarization mode dispersion of the medium comprising:

means for generating polarized light which sequentially has a minimum of three different polarized states, and launching this light into an optical transmission medium, means for measuring the intensities of the light emerging from the optical transmission medium in terms of the elements of a Stokes vector, and for forming a Stokes vector from these measurements, and for repeating these measurements and forming Stokes vectors for each of the states of polarized light launched into the optical transmission medium and at each of two optical angular frequencies of $\omega$ and $\omega+\Delta\omega$;

means for calculating Jones matrices U ($\omega$) and U ($\omega+\Delta\omega$) in the form of unitary matrices which describe the polarization characteristics of the optical transmission medium at the two frequencies $\omega$ and $\omega+\Delta\omega$ using the Stokes vectors determined for each of the different states of polarization at the two frequencies;

means for calculating the 2×2 characteristic hermitian matrix H, where $H \equiv 2i(dU/d\omega)U^+$ of finite differences applied to the Jones matrices U ($\omega$) and U (($\omega+\Delta\omega$);

means for calculating a polarization dispersion vector $\Omega$ from the matrix H;

means for evaluating the polarization mode dispersion for the optical transmission medium, in terms of the differential group delay times of the principal states of polarization $\Delta\tau$ where $\Delta\tau$ is calculated as the norm of the polarization dispersion vector such that $\Delta\tau=|\Omega|$.

15. The apparatus as set out in claim 14 further comprising:

means for normalizing the Stokes such that elements $S_1=Q/I$, $S_2=U/I$ and $S_3=V/I$ are calculated;

means for dividing the light emerging from the optical transmission medium into four portions, and where each portion is directed through a series of optical elements such that the intensities representing the four Stokes elements, I, Q, U, and V are measured separately and simultaneously for each of the different states of polarized light launched into the optical transmission medium.

16. The apparatus as set out in claim 15, wherein a means for calculating renormalized Stokes vectors is provided, wherein $$s_i \equiv \frac{S_i}{\sqrt{S_1^2 + S_2^2 + S_3^2}}, (i = 1, 2, 3)$$

and $S_i$ are the elements of the normalized Stokes vectors, and wherein the means for calculating the Jones matrices $U(\omega)$ and $U(\omega+\Delta\omega)$ uses the renormalized Stokes elements.

17. The apparatus as set out in claim 14, including additional means for calculating the variable η, being the ratio between the imaginary and real parts of the elements of the hermitian matrix H, and further means for adjusting the the size of the frequency difference $\Delta\omega$ such as to cause η to lie in the range $0 \leq |\eta| \leq 1$.

18. The apparatus for measuring polarization mode dispersion, as defined in claim 15, wherein an additional means is provided for calculating the variable η, being the ratio between the imaginary and real parts of the elements of the hermitian matrix H, and means for adjusting the size of the frequency difference $\Delta\omega$ to cause η to lie in the range $0 \leq |\eta| \leq 1$.

19. The apparatus for measuring polarization mode dispersion, as set out in claim 16, including for calculating the variable η, being the ratio between the imaginary and real parts of the elements of the hermitian matrix H, and means for adjusting the size of the frequency difference $\Delta\omega$ to cause η to lie within the range of $0 \leq |\eta \leq |1$.

* * * * *

UNITED STATES PATENT AND TRADEMARK OFFICE
CERTIFICATE OF CORRECTION

PATENT NO. : 5,965,874

DATED : October 12, 1999

INVENTOR(S) : Aso, Osamu, et al

It is certified that error appears in the above-indentified patent and that said Letters Patent is hereby corrected as shown below:

Col. 11, lines 28 and 66: "measurent" should read -- measurement --

Col. 12, line 4: "quantifies" should read -- quantities --

Col. 13, line 38: "$0 \leq \eta \leq 1$" should read $0 \leq \eta \leq 1$,
line 57: "normalizaing" should read -- normalizing --.

Col. 14, line 29: "$S_3$ V/I" should read $S_3 = V/I$,
line 47: "$0 \leq |\rho| \leq 1$" should read $0 \leq |\eta| \leq 1$.

Col. 15, line 31: "y" should read -- $\gamma$ --.

Col. 19, formula 67 should read: $$\frac{d\Delta\phi(\omega)}{d\omega} = 2\sqrt{\left|\frac{du_1}{d\omega}\right|^2 + \left|\frac{du_2}{d\omega}\right|^2} = \Delta\tau(\omega)$$

Col. 20, formula 71 should read $$\Delta\tau = |\Omega| = \sqrt{h_1^2 + |h_2|^2} = 2\sqrt{\left|\frac{du_1}{d\omega}\right|^2 + \left|\frac{du_2}{d\omega}\right|^2},$$

Line 26: "$\rho$" should read -- $\eta$ --,
line 46: "limlted" should read -- limited --.

Col. 21, line 31: "properly" should read -- property --,
line 57: "and , is" should read -- and $\xi$ is --.

UNITED STATES PATENT AND TRADEMARK OFFICE
CERTIFICATE OF CORRECTION

PATENT NO. : 5,965,874
DATED : October 12, 1999
INVENTOR(S) : Aso Osamu, et al

It is certified that error appears in the above-indentified patent and that said Letters Patent is hereby corrected as shown below:

Col. 22, in formula 77, all the term "$1 + S_1$" should read $1 - S_1$.

Col. 23, line 24: "$h = Q\,\Omega_1$" should read -- $h_1 = \Omega_1$ --,
  Line 40: "$\rho$" should read -- $\eta$ --,
  line 46: "$| \leq |\rho| \leq 1$" should read $| \leq |\eta| \leq 1$.

Col. 24, line 37: "$0 \leq \eta\ 1$" should read $0 \leq \eta \leq 1$.

Col. 26, formula (39b) should read $S2 = 2\,\text{Re}\,(\xi_1 \xi_2^*)$.

Col. 27, line 36: "t at" should read -- that --

UNITED STATES PATENT AND TRADEMARK OFFICE
CERTIFICATE OF CORRECTION

PATENT NO. : 5,965,874
DATED : October 12, 1999
INVENTOR(S) : Aso Osamu et al

It is certified that error appears in the above-indentified patent and that said Letters Patent is hereby corrected as shown below:

Col. 29, formula (102): the term $(s_1^A \; s_1^B)$ should read $(s_1^A + s_1^B)$.

Col. 30, formula (103): the exponential part of the element located on first raw, second column of the matrix should read $\exp(-i\gamma_A - i\gamma)$.

Col. 32, line 54, "$\Delta\rho_2$" should read -- $\Delta\tau_2$ --.

Col. 34, line 50: "tot eh" should read -- to the --.

Col. 35, line 36: "$0 \leqq \eta \leqq 1$" should read $0 \leq \eta \leq 1$.

Col. 36, line 42: "fictions" should read -- functions --.

Col. 38, first equation of the column, the exponential part of the element located on first raw, second column of the matrix should read $\exp(-i\gamma_A - i\gamma)$,
    Line 17: "deter ant" should read -- determinant --.

Col. 40, line 32: "polarzed" should read -- polarized --.

Col. 41, line 17: "tie" should read -- the --,
    Line 42: "7" should read -- $\pi$ --,
    line 46: "$\lambda$ 1552" should read -- $\lambda = 1552$ --.

UNITED STATES PATENT AND TRADEMARK OFFICE
CERTIFICATE OF CORRECTION

PATENT NO. : 5,965,874
DATED : October 12, 1999
INVENTOR(S) : Aso Osamu et al

It is certified that error appears in the above-indentified patent and that said Letters Patent is hereby corrected as shown below:

Col. 43, line 9: the equation $h2 = (1.9190+1.2793i)_{10}{}^{-2}$ should read
$h2 = (1.9190+1.2793i)10^{-12}$ Col. 43, in reference 9, last line, "pp. 1283-1292" should read -- pp. 1288-1292 --.

In the claims:

Claim 3: col. 46, equation between lines 20 and 25, the numerator "$S_1$" should read -- $S_i$ --.,
Line 26: "a" should read -- and --,
line 32: "normalized" should read -- renormalized --.

Claim 5: col. 46, line 42: "claim 3" should read -- claim 2 --.

UNITED STATES PATENT AND TRADEMARK OFFICE
CERTIFICATE OF CORRECTION

PATENT NO. : 5,965,874
DATED : October 12, 1998
INVENTOR(S) : Aso Osamu et al

It is certified that error appears in the above-indentified patent and that said Letters Patent is hereby corrected as shown below:

Claim 8: col. 48, line 35: "matrix II" should read -- matrix H --.

Claim 10: col. 48, "$0 \leq |\eta| \leq 1$" should read $0 \leq \eta \leq 1$.

Claim 17, col. 51, lines 13-14: "adjusting the the size" should read -- adjusting the size --,
line 15: "$0 \leq |\eta| \leq 1$" should read $0 \leq \eta \leq 1$.

Claim 18, col. 52, line 7: "$0 \leq |\eta| \leq 1$" should read $0 \leq \eta \leq 1$.

Claim 19, col. 52, line 13: "$0 \leq |\eta \leq 1$" should read $0 \leq \eta \leq 1$.

Signed and Sealed this

Seventeenth Day of April, 2001

*Attest:*

NICHOLAS P. GODICI

*Attesting Officer*    *Acting Director of the United States Patent and Trademark Office*